United States Patent
Corson

(12) 
(10) Patent No.: US 7,635,564 B2
(45) Date of Patent: Dec. 22, 2009

(54) BIOPOLYMERIC ARRAYS HAVING REPLICATE ELEMENTS

(75) Inventor: John F. Corson, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 248 days.

(21) Appl. No.: 11/411,681

(22) Filed: Apr. 25, 2006

(65) Prior Publication Data

US 2006/0188922 A1 Aug. 24, 2006

Related U.S. Application Data

(63) Continuation-in-part of application No. 10/723,374, filed on Nov. 25, 2003, now abandoned, which is a continuation-in-part of application No. 10/281,408, filed on Oct. 25, 2002, now abandoned.

(60) Provisional application No. 60/789,805, filed on Apr. 5, 2006.

(51) Int. Cl.
C12Q 1/68 (2006.01)

(52) U.S. Cl. ......................................................... 435/6

(58) Field of Classification Search ................. None
See application file for complete search history.

(56) References Cited

U.S. PATENT DOCUMENTS

| 5,143,854 | A | 9/1992 | Pirrung et al. |
| 5,445,934 | A | 8/1995 | Fodor et al. |
| 5,601,980 | A | 2/1997 | Gordon et al. |
| 5,985,356 | A | 11/1999 | Schultz et al. |
| 6,057,100 | A | 5/2000 | Heynecker |
| 6,306,599 | B1 | 10/2001 | Perbost |
| 6,448,387 | B1 * | 9/2002 | Slater et al. ................ 536/23.1 |
| 6,599,693 | B1 | 7/2003 | Webb |

FOREIGN PATENT DOCUMENTS

| WO | 9733169 | 9/1997 |
| WO | 0165462 | 9/2001 |
| WO | 0185364 | 11/2001 |
| WO | 02084285 | 10/2002 |
| WO | 02096552 | 12/2002 |
| WO | 03077851 | 9/2003 |

OTHER PUBLICATIONS

Bentwich. FEBS Letters vol. 579:5904-5910. 2005.*
Lappin et al. Journal of Molecular Diagnostics vol. 3:178-188. 2001.*
GB Search Report, Application No. GB0708047.6, mailed Aug. 7, 2007, 1 page, corresponding to U.S. Appl. No. 11/411,681.

* cited by examiner

Primary Examiner—Heather G Calamita

(57) ABSTRACT

A method for designing an array is provided. In certain embodiments, this method includes grouping probes into a plurality of ranked groups of probes; and designing an array comprising the ranked groups of probes, wherein the array contains more replicates of probes in a higher ranked group as compared to probes of a lower ranked group of probes.

10 Claims, 8 Drawing Sheets

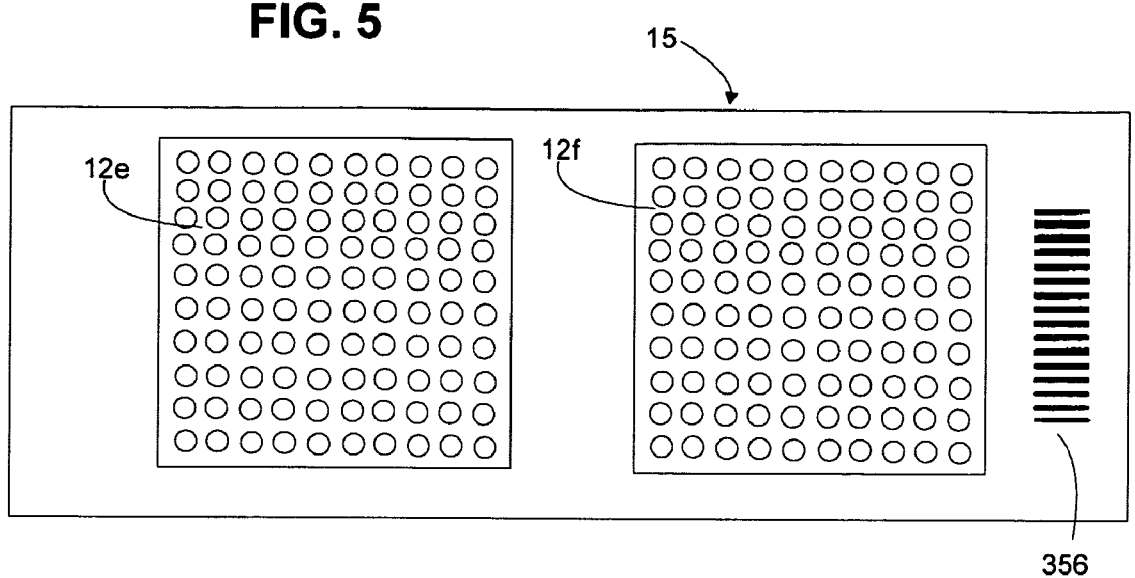
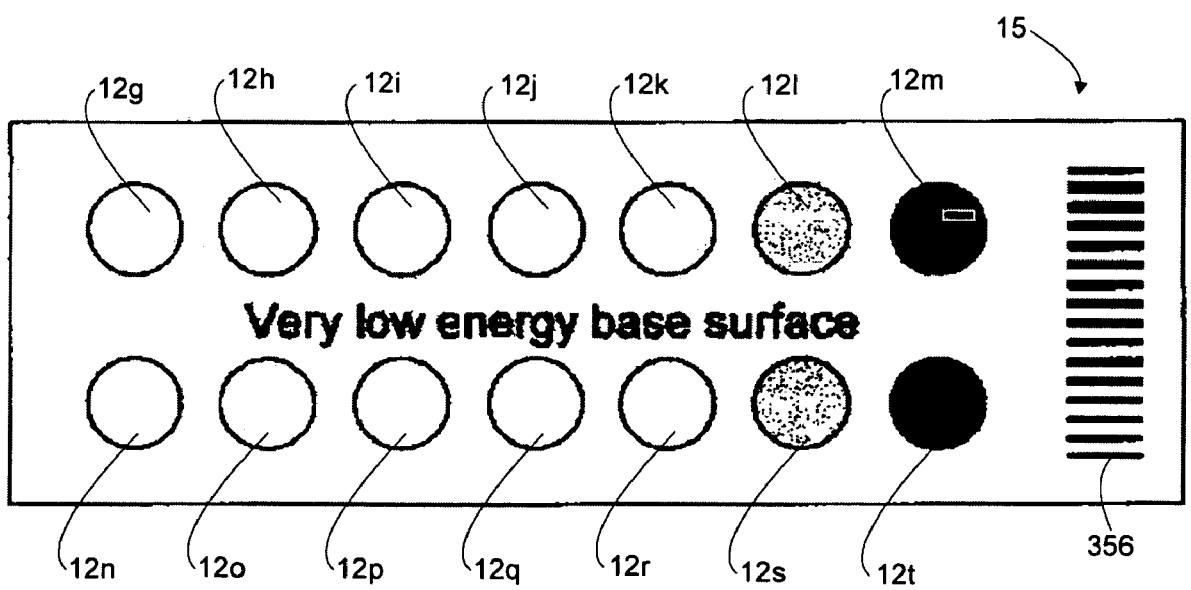

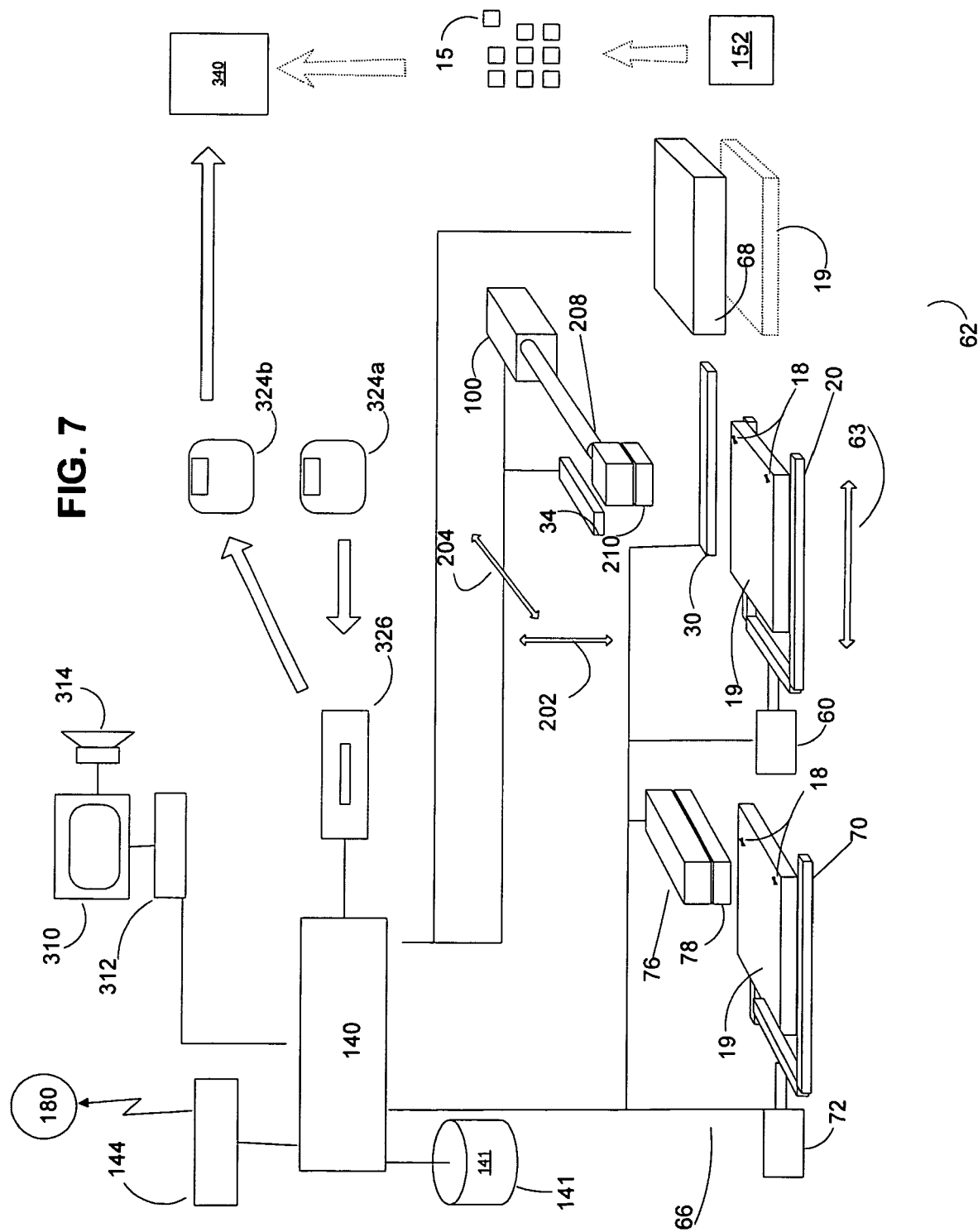

BIOPOLYMERIC ARRAYS HAVING REPLICATE ELEMENTS

CROSS REFERENCE TO RELATED APPLICATIONS

This application: a) claims the benefit of provisional application Ser. No. 60/789,805, filed on Apr. 5, 2006; and b) is a continuation-in-part application of application Ser. No. 10/723,374, filed Nov. 25, 2003, which application is a continuation-in-part application of application Ser. No. 10/281,408, filed Oct. 25, 2002, which applications are incorporated herein by reference in their entirety.

FIELD OF THE INVENTION

The present invention relates to biopolymeric arrays, such as polynucleotide arrays (for example, DNA arrays), which are useful in diagnostic, screening, gene expression analysis, and other applications.

BACKGROUND OF THE INVENTION

In the following discussion and throughout the present application, while various references are cited no cited reference is admitted to be prior art to the present application.

Chemical arrays, such as polynucleotide or protein arrays (for example, DNA or RNA arrays), are known and are used, for example, as diagnostic or screening tools. Polynucleotide arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon reading the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers (such as from synthesis or natural sources) onto a substrate, or by in situ synthesis methods. Methods of depositing obtained biopolymers include loading then touching a pin or capillary to a surface, such as described in U.S. Pat. No. 5,807,522 or deposition by firing from a pulse jet such as an inkjet head, such as described in PCT publications WO 95/25116 and WO 98/41531, and elsewhere. Such a deposition method can be regarded as forming each feature by one cycle of attachment (that is, there is only one cycle at each feature during which the previously obtained biopolymer is attached to the substrate). For in situ fabrication methods, multiple different reagent droplets are deposited by pulse jet or other means at a given target location in order to form the final feature (hence a probe of the feature is synthesized on the array substrate). The in situ fabrication methods include those described in U.S. Pat. No. 5,449,754 for synthesizing peptide arrays, and in U.S. Pat. No. 6,180,351 and WO 98/41531 and the references cited therein for polynucleotides, and may also use pulse jets for depositing reagents. The in situ method for fabricating a polynucleotide array typically follows, at each of the multiple different addresses at which features are to be formed, the same conventional iterative sequence used in forming polynucleotides from nucleoside reagents on a support by means of known chemistry. This iterative sequence can be considered as multiple ones of the following attachment cycle at each feature to be formed: (a) coupling an activated selected nucleoside (a monomeric unit) through a phosphite linkage to a functionalized support in the first iteration, or a nucleoside bound to the substrate (i.e. the nucleoside-modified substrate) in subsequent iterations; (b) optionally, blocking unreacted hydroxyl groups on the substrate bound nucleoside (sometimes referenced as "capping"); (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The coupling can be performed by depositing drops of an activator and phosphoramidite at the specific desired feature locations for the array. A final deprotection step is provided in which nitrogenous bases and phosphate group are simultaneously deprotected by treatment with ammonium hydroxide and/or methylamine under known conditions. Capping, oxidation and deprotection can be accomplished by treating the entire substrate ("flooding") with a layer of the appropriate reagent. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in another flooding procedure in a known manner. Conventionally, a single pulse jet or other dispenser is assigned to deposit a single monomeric unit.

The foregoing chemistry of the synthesis of polynucleotides is described in detail, for example, in Caruthers, Science 230: 281-285, 1985; Itakura et al., Ann. Rev. Biochem. 53: 323-356; Hunkapillar et al., Nature 310: 105-110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, 5,869,643, EP 0294196, and elsewhere. The phosphoramidite and phosphite triester approaches are most broadly used, but other approaches include the phosphodiester approach, the phosphotriester approach and the H-phosphonate approach. The substrates are typically functionalized to bond to the first deposited monomer. Suitable techniques for functionalizing substrates with such linking moieties are described, for example, in U.S. Pat. No. 6,258,454 and Southern, E. M., Maskos, U. and Elder, J. K., Genomics, 13, 1007-1017, 1992. In the case of array fabrication, different monomers and activator may be deposited at different addresses on the substrate during any one cycle so that the different features of the completed array will have different desired biopolymer sequences. One or more intermediate further steps may be required in each cycle, such as the conventional oxidation, capping and washing steps in the case of in situ fabrication of polynucleotide arrays (again, these steps may be performed in flooding procedure).

Further details of fabricating biopolymer arrays by depositing either previously obtained biopolymers or by the in situ method are disclosed in U.S. Pat. Nos. 6,242,266, 6,232,072, 6,180,351, and 6,171,797. In array fabrication, the quantities of polynucleotide available are usually very small and expensive. Additionally, sample quantities available for testing are usually also very small and it is therefore desirable to simultaneously test the same sample against a large number of different probes on an array. These conditions require use of arrays with large numbers of very small, closely spaced features.

In fabricating arrays by depositing previously obtained biopolymers or by the in situ method, typically the entire region on the substrate surface on which an array will be formed (an "array region") is completely exposed to one or more reagents. For example, in either method array regions will often be exposed to one or more linker compositions to form a suitable linker layer on the surface which binds to both the substrate and biopolymer or biomonomer. Particularly useful linker compositions and methods are disclosed in U.S. Pat. Nos. 6,319,674 and 6,444,268 which may use various silane based compounds as linkers or other surface modifying agents (for example, to modify the surface energy to control deposited drop spread). The solution containing the silane compounds is exposed to a substrate surface in a reactor.

An array is typically read such as by detecting light emitted from features in response to an interrogating light. A typical detector may be a photomultiplier tube ("PMT"). However, the concentration of the various target polynucleotides (or other targets) in a sample is not always known in advance. On the other hand, the present invention now recognizes that each feature can only quantitatively measure a limited range of target concentrations (sometimes referenced herein as the "dynamic range" of a feature). For example, features having a higher probe density tend to be relatively insensitive to changes in target concentrations at lower levels whereas features having a lower probe density tend to be relatively insensitive to changes in target concentration at higher levels.

As with all measurement systems, the detection system of a biopolymeric array system, which includes the array itself, labeling components, scanning/imaging apparatus, etc., has a particular signal to noise ratio. In order to obtain meaningful assay results, the signal to noise ratio must be within a certain range. In general, the signal to noise ratio decreases as signal decreases. However, when the signal to noise ratio falls below a certain level, array assay results may be compromised or meaningless in certain instances because it will not be possible to distinguish signal from system noise. For example, in certain instances a particular target may be present in the sample in such a small amount that when the sample is used with an array in an array assay the low signal obtained from the probe/target complex may provide a signal to noise ratio that is at a level below where signal cannot be meaningfully distinguished from noise in the system. Likewise, in certain instances signal may be higher than a system's detection limit.

Accordingly, there continues to be an interest in the development of array systems in which meaningful data may be obtained when used with targets present in a range of amounts, e.g., very low to very high abundance targets. The present invention recognizes that it would be desirable to extend the dynamic range over which changes in a target concentration can be detected by a chemical array.

SUMMARY OF THE INVENTION

A method for designing an array is provided. In certain embodiments, this method includes grouping probes into a plurality of ranked groups of probes; and designing an array comprising the ranked groups of probes, wherein the array contains more replicates of probes in a higher ranked group as compared to probes of a lower ranked group. Within each group of probes, the number of probe replicates may be determined by a predetermined criterion, e.g., the anticipated abundance of target for the probe in a sample. The anticipated abundance of a target may be based on experimental data.

The probes may be grouped according to a selected criterion. In certain embodiments, the probes are grouped according to location, function or expression. In other embodiments, the probes may be arbitrarily grouped, grouped by customer input, or grouped using experimental data.

A computer readable medium comprising instructions for performing the method are provided, as is a computer executable method for designing an array. The computer readable medium may include programming for designing an array comprising ranked groups of probes, wherein the programming provides for design of an array that contains more replicates of probes in a higher ranked group as compared to probes of a lower ranked group of probes. The computer readable may be comprised by a computer.

The computer executable method for designing the array may include: a) inputting grouping information so that probes can be grouped into ranked groups of probes; b) accessing the above-described computer readable medium; and c) executing the programming, to design the array. Inputting may be done using a user interface, and may be done at a location that is remote to the location in which the programming is executed. The method may further comprise receiving an array design, fabricating the designed array, or receiving the designed array.

Also provided is a method of fabricating an array. This method includes designing an array according to the subject array-design method and fabricating the array. An array fabricated by this method is provided.

An array comprising ranked groups of probes, wherein the array contains more replicates of probes in a higher ranked group as compared to probes of a lower ranked group of probes is also provided. Within each group of probes, the number of probe replicates may be determined by the anticipated abundance of target for the probe in a sample in some embodiments.

A method of sample analysis is also provided. This method may include: a) contacting a subject array with a sample; and b) evaluating binding of the sample to the probes.

Methods of preparing biopolymeric arrays are provided. Certain embodiments of the subject methods include immobilizing at least a first population of a number of copies of a first probe for a first target to a surface of a solid support, wherein the number of probe copies of the first population is dependant on the at least suspected abundance of the target in a sample for which the array is designed. Also provided are biopolymeric arrays that include at least a first population of a number of copies of a first probe for a first target immobilized on a surface of a solid support, wherein the number of probe copies is dependant on the at least suspected abundance of the target present in a sample for which the array is designed to assay. The subject invention also includes algorithms present on computer readable mediums and kits for use in practicing the subject methods.

The present invention also provides one or more arrays of multiple chemical probes bound to a surface of a substrate at different features of the array. The arrays may have features of different probe composition (for example, at least ten such features) which are repeated at different probe density.

In one configuration of the one or more arrays of the present invention, different regions (for example, at least two or three regions) of the surface each may each have multiple features (for example, at least ten or at least one hundred) with a same probe density within a region and the different regions have different probe densities. These different regions may also have different linker agent densities, the probes being bound to the different regions through the linker agent.

The one or more arrays of the present invention may be provided as a component of an array assembly which has an associated indication of features having different probe densities of a same probe composition. The associated indication can, for example, comprise one or more identifiers on the substrate which carry the indication or one or more identifiers on the array which is linked to a file which carries the indication.

The present invention further provides a method of producing a surface modified substrate. This method includes comprising contacting different regions of the substrate surface to a linking agent under different conditions (for example, by contacting those different regions with fluids having different linking agent concentrations) so that the linking agent binds to the different regions at different densities.

There is also provided by the present invention, a method of fabricating one or more arrays of multiple chemical probes bound to a surface of a substrate at different features of the array. This method may include contacting different probes or probe precursors (for example, at least ten or one hundred of them) with different locations on the substrate surface, so that each of the probes or probe precursors binds to the different locations through the linker agent. The foregoing can be repeated as needed so as to form the one or more arrays with features of diff The present invention further provides a method which includes reading one or more chemical arrays of the present invention, each of which has been exposed to a sample, to obtain signal data from the features. The signal data from the features of the same probe composition but with different probe densities, may then be merged.

There is further provided by the present invention, apparatus, and computer program products, which can execute one or more methods of the present invention for making substrates or arrays, or for reading arrays.

The various aspects of the present invention can provide any one or more of the following and/or other useful benefits. For example, arrays can be provided which can detect a target for a particular probe over a high dynamic range.

BRIEF DESCRIPTION OF THE DRAWINGS

FIGS. 5 and 6 show some different array assemblies of the present invention;

FIG. 7 illustrates an apparatus of the present invention which can execute a method of the present invention for producing a substrate or fabricating arrays.

Figure 1:
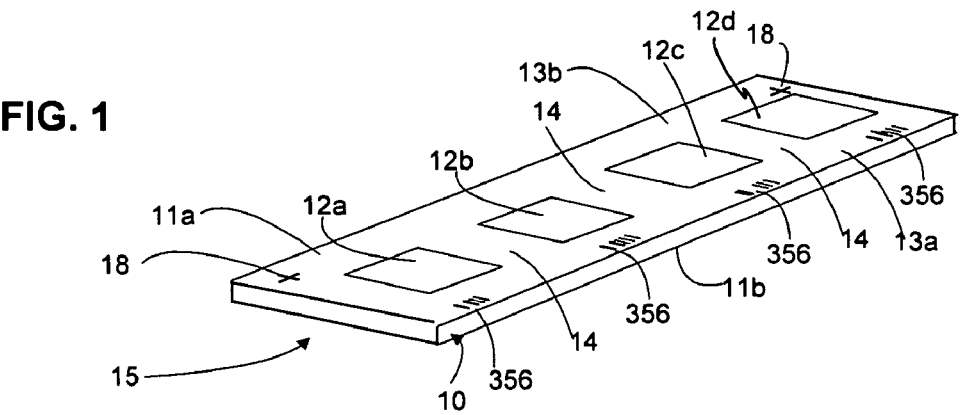
FIG. 1 illustrates an array assembly carrying multiple arrays, such as may be fabricated by methods of the present invention.

To facilitate understanding, the same reference numerals have been used, where practical, to designate the same elements that are common to the figures. Different letters after the same number indicate members of a generic class (for example, arrays 12a, 12b may be collectively referred to as "arrays 12"). Drawings are not necessarily to scale.

DEFINITIONS

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one, two or three-dimensional arrangement of addressable regions bearing a particular chemical moiety or moieties (for example, biopolymers such as polynucleotide sequences) associated with that region. Each region may extend into a third dimension in the case where the substrate is porous while not having any substantial third dimension measurement (thickness) in the case where the substrate is non-porous. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). An array feature is generally homogenous and the features typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" or "array characteristics", refers to one or more physical, chemical or biological characteristics of the array, such as feature positioning, one or more feature dimensions, or some indication of an identity or function (for example, chemical or biological) of a moiety at a given location, or how the array should be handled (for example, conditions under which the array is exposed to a sample, or array reading specifications or controls following sample exposure). "Hybridizing" and "binding", with respect to polynucleotides, are used interchangeably.

A "plastic" is any synthetic organic polymer of high molecular weight (for example at least 1,000 grams/mole, or even at least 10,000 or 100,000 grams/mole.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

A "web" references a long continuous piece of substrate material having a length greater than a width. For example, the web length to width ratio may be at least 5/1, 10/1, 50/1, 100/1, 200/1, or 500/1, or even at least 1000/1.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "assembly" may be the array plus only a substrate on which the array is deposited, although the assembly may be in the form of a package which includes other features (such as a housing with a chamber). A "chamber" references an enclosed volume (although a chamber may be accessible through one or more ports). It will also be appreciated that throughout the present application, that words such as "front", "back", "top", "upper", and "lower" are used in a relative sense only. "Fluid" is used herein to reference a liquid. Reference to a singular item, includes the possibility that there are plural of the same items present. "May" refers to optionally. Any recited method can be carried out in the ordered sequence of events as recited, or any other logically possible sequence.

A "pulse jet" is any device which can dispense drops in the formation of an array. Pulse jets operate by delivering a pulse of pressure (such as by a piezoelectric or thermoelectric element) to liquid adjacent an outlet or orifice such that a drop will be dispensed therefrom.

A "linking layer" bound to the surface may, for example, be less than 200 angstroms or even less than 10 angstroms in thickness (or less than 8, 6, or 4 angstroms thick). Such layer may have a polynucleotide, protein, nucleoside or amino acid minimum binding affinity of 104 to 106 units/$\mu$2. Layer thickness can be evaluated using UV or X-ray ellipsometry.

"Continuous" in reference to an area on the substrate surface references an area which is uninterrupted by any gaps within that area. The distinct features of an array may then be formed on such a continuous area.

A "group" in relation to a chemical formula, includes both substituted and unsubstituted forms of the group.

"Lower alkyl group" is an alkyl group with from 1 to 6 C atoms, and may only have any one of 1, 2, 3, or 4 C atoms.

"Surface energy" is as defined in U.S. Pat. No. 6,444,268.

A "region" on a substrate surface is a continuous area on that surface, with different regions not overlapping one another. Typically, a particular region will contain multiple features (such as at least ten, at least fifty, at least one or two hundred, or at least one thousand) of the same probe density. Each region may have an area of at least 1 mm2, or at least 10 mm2, at least 100 mm2, or at least 200 mm2.

"Linker agent density" or "capping agent density" refers to the number of linker molecules or capping molecules per unit area. Linker agents are counted in determining linker agent density whether or not they are linked to probes or are themselves capped. For capping agent density only capping agents directly attached to the substrate surface are counted in the capping agent density. Linker agent density within a region includes linker agent within any interfeature areas, and will typically be relatively uniform over a given region, although there may be some minor variation. If different regions on a substrate surface of uniform composition are exposed under the same conditions to a same composition of linking agent which binds to the surface, the linker agent density in the regions will be considered to be the "same". These terms are used interchangeably with, and have the same means as, "region linker agent density" and "region capping agent density".

"Probe density" is a shorthand way of referring to the number of linker molecules or probe molecules per unit area within a feature. This term then is used interchangeably with, and has the same meaning as "feature probe density". Thus, any interfeature areas which are essentially devoid of the probe are not taken into consideration in determining a probe density. "Probe density" in a region then, is distinct and independent of feature density (which is the number of features per unit area).

A different linker agent density, different capping agent density, or different probe density means the average linker agent, capping agent, or probe density over the area referenced differs by more than 5%, for example more than 10%, 15%, 20% or 50%. A "same" density of any of the foregoing means that the average linker agent, capping agent, or probe density over the area referenced differs by less than 20%, for example no more than 10%, 5%, 2% or 1%

The steps of any method herein may be performed in the recited order, or in any other order that is logically possible. All patents and other references cited in this application, are incorporated into this application by reference except insofar as anything in those patents or references, including definitions, conflicts with anything in the present application (in which case the present application is to prevail).

"Optional" or "optionally" means that the subsequently described circumstance may or may not occur, so that the description includes instances where the circumstance occurs and instances where it does not.

The terms "target" "target molecule" "target biomolecule" and "analyte" are used herein interchangeably and refer to a known or unknown molecule in or suspected of being in a sample. A target is one that will bind, e.g., hybridize, to a probe on a substrate surface if the target molecule and the molecular probe are complementary, e.g., if they contain complementary regions, i.e., if they are members of a specific binding pair.

The term "probe" as used herein refers to a molecule of known identity adherent to a substrate.

"Probe copies" refers to exact copies of a given probe.

The term "rigid" is used herein to refer to a structure that does not readily bend without breakage, i.e., the structure is not flexible.

The term "hybridization" as used herein refers to binding between complementary or partially complementary molecules, for example as between the sense and anti-sense strands of double-stranded DNA. Such binding is commonly non-covalent binding, and is specific enough that such binding may be used to differentiate between highly complementary molecules and others less complementary. Examples of highly complementary molecules include complementary oligonucleotides, DNA, RNA, and the like, which comprise a region of nucleotides arranged in the nucleotide sequence that is exactly complementary to a probe; examples of less complementary oligonucleotides include ones with nucleotide sequences comprising one or more nucleotides not in the sequence exactly complementary to a probe oligonucleotide.

The term "hybridization solution" or "hybridization reagent" used herein interchangeably refers to a solution suitable for use in a hybridization reaction.

The term "stringent hybridization conditions" as used herein refers to conditions that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding mRNA analytes present in the sample. An example of stringent hybridization conditions is hybridization at 60° C. or higher and 3×SSC (450 mM sodium chloride/45 mM sodium citrate). Another example of stringent hybridization conditions is incubation at 42° C. in a solution containing 30% formamide, 1M NaCl, 0.5% sodium sarcosine, 50 mM MES, pH 6.5. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The term "ligand" as used herein refers to a moiety that is capable of covalently or otherwise chemically binding a compound of interest. Ligands may be naturally-occurring or manmade. Examples of ligands include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, and proteins.

The term "receptor" as used herein is a moiety that has an affinity for a ligand. Receptors may be naturally-occurring or manmade. They may be employed in their unaltered state or as aggregates with other species. Receptors may be attached, covalently or noncovalently, to a binding member, either directly or via a specific binding substance. Examples of receptors include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, and organelles. Receptors are sometimes referred to in the art as anti-ligands. As the term receptors is used herein, no difference in meaning is intended. A "Ligand Receptor Pair" is formed when two molecules have combined through molecular recognition to form a complex.

The term "sample" as used herein relates to a material or mixture of materials, typically, although not necessarily, in fluid form, containing or suspected of containing one or more components (targets) of interest.

A "computer-based system" refers to the hardware means, software means, and data storage means used to analyze the information of the present invention. The minimum hardware of computer-based systems as they relate to the present invention include a central processing unit (CPU), input means, output means, and data storage means. A skilled artisan can readily appreciate that any one of the currently available computer-based system are suitable for use in the present invention. The data storage means may include any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats may be used for storage, e.g. word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION

As noted above, a method for designing an array is provided. In certain embodiments, this method includes grouping probes into a plurality of ranked groups of probes; and designing an array comprising the ranked groups of probes, wherein a higher ranked group of probes has a greater average number of features per probe on the array than a lower ranked group.

Methods of preparing biopolymeric arrays are provided. The subject methods may include immobilizing at least a first population of a number of copies of a first probe for a first target to a surface of a solid support, wherein the number of probe copies of the first population is dependant on the at least suspected abundance of the target in a sample for which the array is designed. Also provided are biopolymeric arrays that include at least a first population of a number of copies of a first probe for a first target immobilized on a surface of a solid support, wherein the number of probe copies is dependant on the at least suspected abundance of the target present in a sample for which the array is designed to assay. The subject invention also includes algorithms present on computer readable mediums and kits for use in practicing the subject methods.

Turning now to arrays of the present invention, these may have multiple features of higher probe density which are formed on a region of higher linking agent density and multiple features of lower probe density are formed on a region of lower linking agent density. Different regions of different linking agent density may also have a capping agent present, with a lower density of capping agent at a region which has a higher density of linker agent. The number of different regions may be at least two, at least three, at least four, at least five, or at least ten. The number of features of different probe composition which are present on each region of higher linking agent density and which features are repeated at a lower probe density on a region of lower linking agent density, may be at least five, at least ten, at least one hundred, or at least one or two thousand.

As to methods of the present invention for producing a surface modified substrate, such methods may also include contacting the different regions on the substrate surface with a capping agent. The capping agent will also bind to the different regions to produce a substrate surface having both linking agent and capping agent bound to the different regions with a lower density of capping agent at a region which has a higher density of linking agent. However, the capping agent will not bind to a subsequently deposited probe and so it "caps" or blocks any reactive sites on the substrate surface. The capping agent may be in a fluid different from that containing the linking agent which contacts the substrate surface, or may be in the same fluid as the linking agent with, for example, a fluid with a higher concentration of linking agent containing a lower concentration of capping agent. In any event, one way of contacting the fluids containing the linking agent or capping agent is by depositing drops of the fluid to be deposited at the different regions so that the drops for each region together continuously cover that region.

The probes of the arrays may be any biopolymer, such as polynucleotides or amino acid polymers (which term is used to include peptides and proteins). During array fabrication, a same concentration of a same probe or probe precursor may be used to contact the locations of repeated features of different feature size, different probe density, different probe copy number, etc, where such may be determined at least in part by the at least suspected abundance of a target in a sample to which the array is designed to assay. For example, when the foregoing different locations of repeated features are in different regions with a different density, feature size, probe copy number, etc., of a same or different linking agent, this will result in features of a probe composition which are repeated in the different regions at different feature probe density, feature size, probe copy number, etc. During array fabrication, a same concentration of a same probe or probe precursor may be used to contact the locations of repeated features of the same feature size, same probe density, same probe copy number, etc, where such may be determined at least in part by the at least suspected abundance of a target in a sample to which the array is designed to assay. This is one way to provide the different regions each with the features of a same feature probe density, same feature size, same probe copy number, and the like.

Arrays may also be fabricated which, as already described, may have different regions with different densities of a same or different linker agent present (to which probes will be bound) and optionally, capping agent (to which probes will not bind), where such may be determined at least in part by the at least suspected abundance of a target in a sample to which the array is designed to assay. Since the different regions may have different surface energy levels and therefore different contact angles with drops of the same composition comprising the probe or probe precursors, drops of a larger volume may be deposited on one of the regions having a higher contact angle than are deposited at another one of the regions having a lower contact angle. This may help reduce disparity in feature areas in the different regions.

The apparatus of the present invention may include a substrate holder on which the substrate can be mounted, and a drop deposition system to deposit drops of the probes or probe precursors. A processor controls the drop deposition system so as to contact each of the different probes or probe precursors with different locations on the substrate surface, and repeat this as needed, so as to form the array. The processor may also receive an indication of the location of different regions on a substrate to which probes or probe precursors will bind with different density, and controls the drop deposition system to form the array with features of different probe composition in one of the regions which are repeated in another of the regions at a different probe density.

Computer program products of the present invention may include a computer readable storage medium having a computer program stored thereon which controls the apparatus to perform a method as described herein. Any computer readable storage medium for any purpose herein may include, for example, an optical or magnetic memory (such as a fixed or portable disk or other device), or a solid state memory.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

Array Design Methods

Certain embodiments of the subject array design methods include designing an array comprising ranked groups of probes, where the array contains more probe replicates (i.e., more independent features containing the same probe) for probes in higher ranked groups, as compared to a lower ranked group. In certain embodiments, within each group of probes, the number of probe replicates may determined by the anticipated abundance of target for the probe in a sample. In certain embodiments, an array contains more probes for less abundant targets than probes for more abundant targets.

Depending on the number of features of the array to be designed, the number of different probes available and the desired number of probe replicates, the probes may be grouped into a plurality of groups, where a plurality is at least 2 (e.g., at least 3, at least 5, at least 10, at least 20, at least 50, or at least 100, up to about 1,000, 10,000 or more). Each group may contain a variable number of probes, or the same number of probes, and, in certain embodiments, may contain at least 50 (e.g., at least 100, at least 500, at least 1,000, at least 5,000 or at least 10,000 probes, up to about 50,000 or more) probes. The relative number of the probes in each group may vary or may be the same.

The probes may be grouped according to any suitable criteria.

In one embodiment, the probes may be grouped by location, e.g., by their binding to particular areas of a genome. For example, the probes may be grouped by their binding to particular chromosomes, (e.g., any of the autosome or sex chromosomes), or by their binding to particular types of features, e.g., promoters, CpG islands, protein coding sequences, miRNA- or cDNA-encoding sequences, exons or introns, etc. In one embodiment, the probes may be grouped by the chromosome to which they bind, or by the type of feature to which they bind.

In another embodiment, the probes may be grouped according to the function of the genes to which they bind. For example, the probes may be grouped according to the role of the genes to which they bind in development of a phenotype, e.g., a cancerous phenotype, in a particular aspect of cell biology, e.g., a role in the cell cycle or signal transduction. In one embodiment the probes are grouped according to their enzymatic activities, e.g., whether they are a phosphatase, kinase, or are involved in the production of signaling molecules.

In a further embodiment, the probes may be grouped according to the expression pattern of the targets to which the probes bind. For example, the probes may be grouped according to the differences in expression of the targets in response to a stimulus (e.g., a chemical, biological or environmental stimulus), or in different cells (e.g., diseased cells and normal cells, cancerous cells and normal cells, differentiated cells and non-differentiated cells, cells of different tissues, etc). In one embodiment, the probes are grouped according to the relative abundance of targets for the probes in one or more, e.g., one or two samples. For example, the probes may be grouped as binding to targets that are, for example, highly induced, moderately induced, moderately repressed, highly repressed, or neither induced nor repressed, or any increment therebetween.

As would be apparent from the above, in certain cases the probes may be grouped in accordance with experimental data obtained using the probes. As such, in one embodiment, the instant methods may include obtaining experimental data for a set of probes and then grouping the probes in accordance with the experimental data, prior to array designing the array.

In other embodiment, the probes may be grouped arbitrarily. As will be discussed in greater detail below, the probes maybe grouped by customer input. In these embodiments, a customer may input grouping information, and an array may be designed according to the instant methods, using the grouping information supplied by the customer.

In certain embodiments, the groups are ranked, i.e., scored, such that the groups can be distinguished by their ranking. The groups may be ranked by any suitable criteria. Depending on how the probes were grouped and the desired results, the groups of probes could be ranked according to the size of the difference in the amount of the targets for the probes in two samples. For example, probes for highly induced and highly repressed targets may be highly ranked, probes for moderately induced and moderately repressed targets may be moderately ranked and probes for targets that are neither induced nor repressed may be ranked lowest.

In certain embodiments, the probe groups may be arbitrarily chosen. As will be discussed in greater detail below, the probe groups maybe ranked by customer input. In these embodiments, a customer may input the ranking of a group in addition to the grouping information, and an array may be designed according to the instant methods using the grouping and ranking information supplied by the customer.

In certain embodiments, the groups are ranked according to the how interested a customer is in obtaining data for probes within the different groups. For example, the group that the customer is most interested in may be ranked highest, whereas the group that the customer is least interested in may be ranked lowest.

The exact ranking system may vary greatly. In certain embodiments, the ranking system may be a numerical ranking system in which, for example, the highest ranked group is indicated by the highest number and the lowest ranked group is indicated by the lowest number. As will be described in greater detail below, the number indicating the ranking of a group may be employed in an array design algorithm to calculate the number of replicates for the probes of that group of probes. In one embodiment, the higher the number indicating the ranking of a group, the more the probes of that group are replicated in the designed array.

Once the probes of an array are grouped into a plurality of ranked groups of probes, an array that contains the groups of probes is designed. The designed array contains a greater number of probe replicates (i.e., a greater number independent features containing the same probe) for probes of the highest ranked group, and the least number of probe replicates for probes of the lowest ranked group. Probes of lesser ranked groups are replicated in fewer number than the probes of higher ranked groups. Conversely, probes of higher ranked groups are replicated in higher number than the probes of lower ranked groups. In certain embodiments, the average number of replicates for probes in higher ranked groups is higher than the average number of probe replicates of probes in lower ranked groups. In one embodiment, the average number of probe replicates in each probe group may be proportional to the number used to rank the group. For example, if the highest ranked group is ranked by the number 8, a medium ranked group is ranked by the number 4, and the lowest ranked group is ranked by the number 2, then the average number of replicates of probes in the highest ranked group may be twice that of the medium ranked group and four times that of lowest ranked group.

In certain embodiments, the average number of a replicates of a probe in the highest ranked group may be at least about 5, e.g., at least about 10, at least about 20, at least about 50, at least about 100, up to about 200, up to about 500, or up to about 1000, or more. In certain embodiments, the average number of a replicates of a probe in the lowest ranked group may be at least 1, e.g., at least 2, at least about 5, at least about 10, up to about 5, up to about 10, or up to about 20, or more. Probes in intermediate ranked groups are replicated at an average number that is between the average number of the highest ranked group and the average number of the lowest ranked group. In designing the array, the probe replicates may be interspersed throughout the array or present in the same area. In one embodiment, probes in the highest ranked group are replicated at least 8 times more, e.g., at least 10, at least 20 or at least 50 times more than the probes of the lowest ranked group.

In certain embodiments, the ranked probe group-based methods described above may be combined with other probe design methods, described in greater detail below, in which the number of probe replicates is determined by the anticipated abundance of target for the probe in a sample. In these embodiments, each probe within a group of probes is replicated in accordance with the anticipated abundance of target for that probe in the sample to be tested. In one array design method, within a single probe group, the probes that are anticipated to detect low abundance targets are replicated at lower number than probes that are anticipated to detect high abundance targets.

As is described in greater detail below, the anticipated abundance of a target for a probe may be experimentally determined. Accordingly, in one embodiment, the instant method includes producing data on the abundance of a target for a probe in a sample, and then designing an array according to the instant methods using the data.

In certain embodiments and depending on which group a probe is in, the number of replicates for a probe for a low abundance target may be at least about 2, e.g., at least about 5, at least about 10, at least about 20, at least about 50, at least about 100, up to about 200, up to about 500, or up to about 1000, or more. The number of replicates for a probe for a high abundance target may be at least about 2, e.g., at least 2, at least about 5, at least about 10, up to about 5, up to about 10, or up to about 20, or more. Within each group, probes for intermediate abundance targets are replicated at numbers that are between the number of replicates for a probes for a high and low abundance targets. In designing the array, the probe replicates may be interspersed throughout the array or present in the same area. In one embodiment, probes for the lowest abundance targets are replicated at least 8 times more, e.g., at least 10, at least 20 or at least 50 times more than the probes of the highest abundance targets.

In certain embodiment, arrays designed by the methods described above contain a plurality of ranked groups of probes, where: a) there are more replicates of the probes of the higher ranked groups, than the lower ranked groups, and b) within each group of probes, the are more replicates of probes for low abundance targets than probes for high abundance targets. The number of different groupings may vary, e.g., may be two or more, three or more, four or more, five or more, etc., different groupings.

Figure 9:
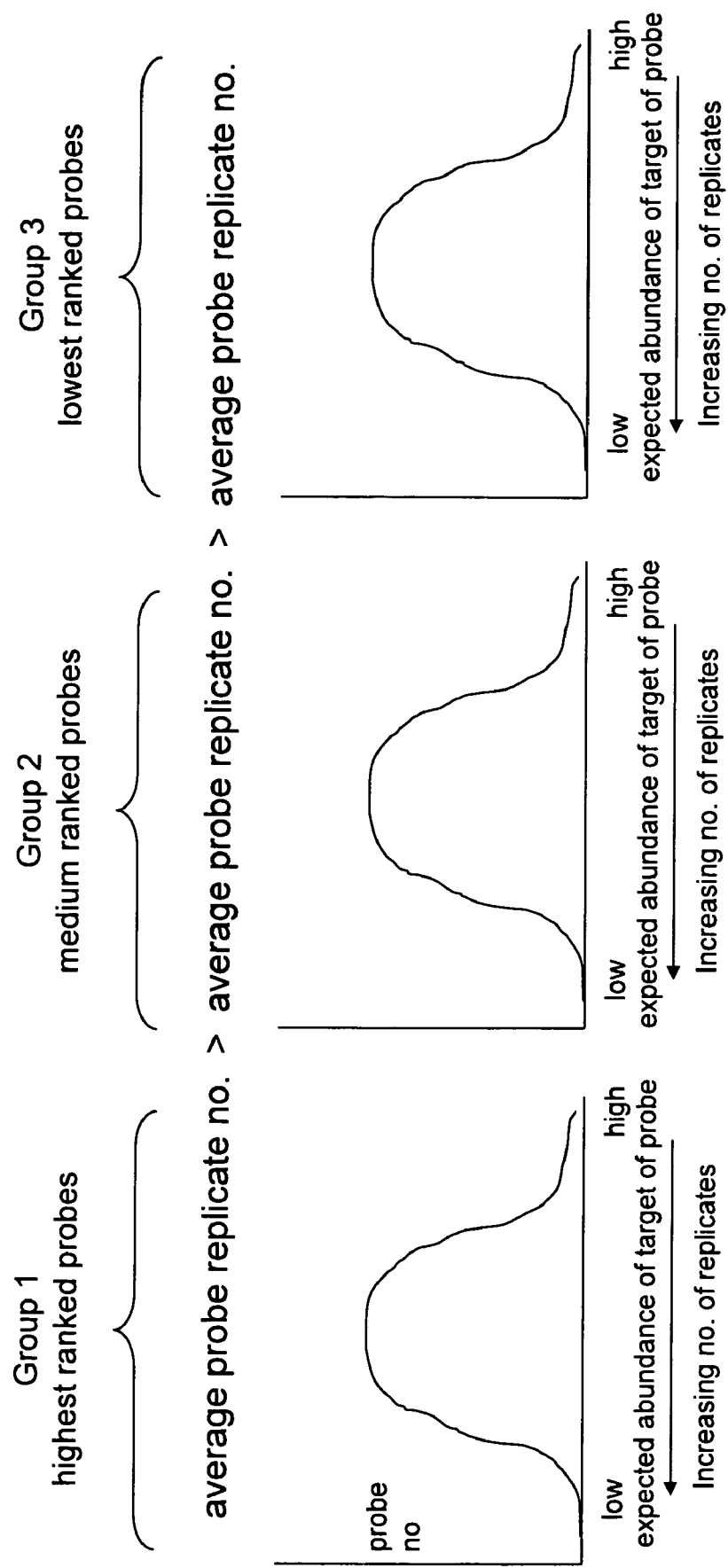
FIG. 9 is three graphs illustrating the distribution of probe replicates in an array containing three groups of probes.

The distribution of the number of replicates of probes in one embodiment is illustrated in FIG. 9. In this embodiment, the probes of an array are grouped into three ranked groups, Group I, Group II and Group III. The average probe replicate number is higher for Group I probes than for Group II probes, and the average probe replicate number is higher for Group II probes than for Group III probes. Within each group of probes, the number of replicates for each probe decreases with the expected abundance of the target for that probe.

As would be apparent, the above method may be performed using an algorithm that may be employed as part of an array design system. In certain embodiments, the algorithm may be part of an array design module of a larger computer-based system for designing arrays. In one embodiment, the system may be used to design arrays in response to an array user's needs. The system may be employed as part of an array fabricator-array user relationship (e.g., a supplier or vendor-customer relationship).

Given the total number of available spaces for probes on a substrate (i.e., the number of addressable features of the substrate) and the grouping information for the probes of the array (i.e., information on which probes are in each group and the ranking of the groups), the algorithm can calculate how many times each probe is to be replicated on the array. In certain embodiments, the algorithm may also calculate how many times each probe is to be replicated on the array using the expected abundance of the targets for the probe, in addition to the grouping in formation for the probes, as discussed above. In addition to calculating the number of replicates, the algorithm may also determine the positioning of the probes on the array.

In one embodiment, an array user may enter grouping information into an interface of a computer-based system and the above-discussed algorithm may be executed. The output of the algorithm may contain information on the probes, and the number of times each of the probes is to be replicated on an array. The interface may be remote or at the same location to the computer readable medium storing instructions for performing the algorithm.

In one embodiment, a user (e.g., a customer) may obtain data using a first array (e.g., an off-the-shelf, stock or catalog array) in which the probes are not replicated according to any grouping information. The user may rank the probes on the first array according to the data obtained using the array, and then group the probes into ranked groups. The grouping information may be used to design a custom array (i.e., an array that is tailored to the user's needs or interests) that has more replicates of higher-ranked probes, fewer replicates of lower-ranked probes and, in certain embodiments, more replicates of probes that are for lower abundance targets and few replicates of probes that are for higher abundance targets. The custom array may be designed by an array vendor, for example. In another embodiment, a user may not obtain data using a first array. In one embodiment, the user simply groups and ranks the probes according to how interested the user is in obtaining data from those probes, and a custom array is designed that has more features of the more interesting probes, and less features of the less interesting probes.

In certain embodiments, in addition to the grouping information, an array user may also enter information on the abundance of targets for the probes on the array. This may be done, for example, by entering a signal distribution, or a signal to noise ratio, for each of the probes. In the absence of this information being entered by a user, the expected abundance of target for each probe in a sample may be estimated by, for example, using other information available to the array design program. The array design system may use this information in calculating how many replicates of each probe are to be present in the designed array.

The user may, at any time, enter information on new probes (i.e., probes that are not present on the first array), as well as the groups to which those new probes belong, to provide a custom array containing those probes. The entry of information may be through any convenient interface, such as, for example an interface that allows tables (e.g., tab delimited tables) to be input into the interface, as well as a field for designating how group of probes are ranked.

Given the total number of array features, the number of different probes available and their grouping information, the algorithm may determine the replicate number for each of the probes in probe groups, in accordance with the above. For instance, in one embodiment, the probes are grouped into three groups, and given a ranking of 8, 4 and 2, where 8 ranks the highest ranked group and 2 ranks the lowest ranked group. The rankings indicate the average probe replicate number for probes in each group. For example, probes in the highest ranked are replicated, on average, 8 times each, whereas probes of the lowest ranked group are replicated, on average, twice each. In one embodiment the number of replicates of each probe may be altered by dividing the number that ranks the group to which the probe belongs (i.e., 8, 4 or 2) by an evaluation of the expected abundance of the probe. For example, a probe in the highest ranked group has 8 replicates. If the target for that probe has an expected abundance of 2 times the average abundance of probes in the same group, then that probe may be replicated four times in the final array designing (8/2=4), leaving 4 spaces to be filled by other probes having lower abundance targets. Similar methods employing the square root, log or other metric for adjusting the number of replicates based on expected target abundance are readily envisioned. In one embodiment, for example, a system that relies on the square root is employed. In this embodiment, a probe that emits a signal that is twice as bright as the average probe has a quarter of the average number of replicates, and a probe that emits a signal that is a third of the average probe is replicated nine times more than the average number of replicates.

In one embodiment, the algorithm may be incorporated into an array design system such as that described in Ser. No. 11/349,425, filed Feb. 6, 2006, which is incorporated herein by referenced in its entirety.

In accordance with the above, a system for producing an array layout is provided. Certain embodiments of the subject system generally includes the following components: (a) a communications module for facilitating information transfer between the system and one or more users, e.g., via a user computer, as described below; and (b) a processing module for performing one or more tasks in response to information received via the communications module of the system. In certain embodiments, the subject systems may be viewed as being the physical embodiment of a web portal, where the term "web portal" refers to a web site or service, e.g., as may be viewed in the form of a web page, that offers a broad array of resources and services to users via an electronic communication element, e.g., via the Internet.

Figure 10:
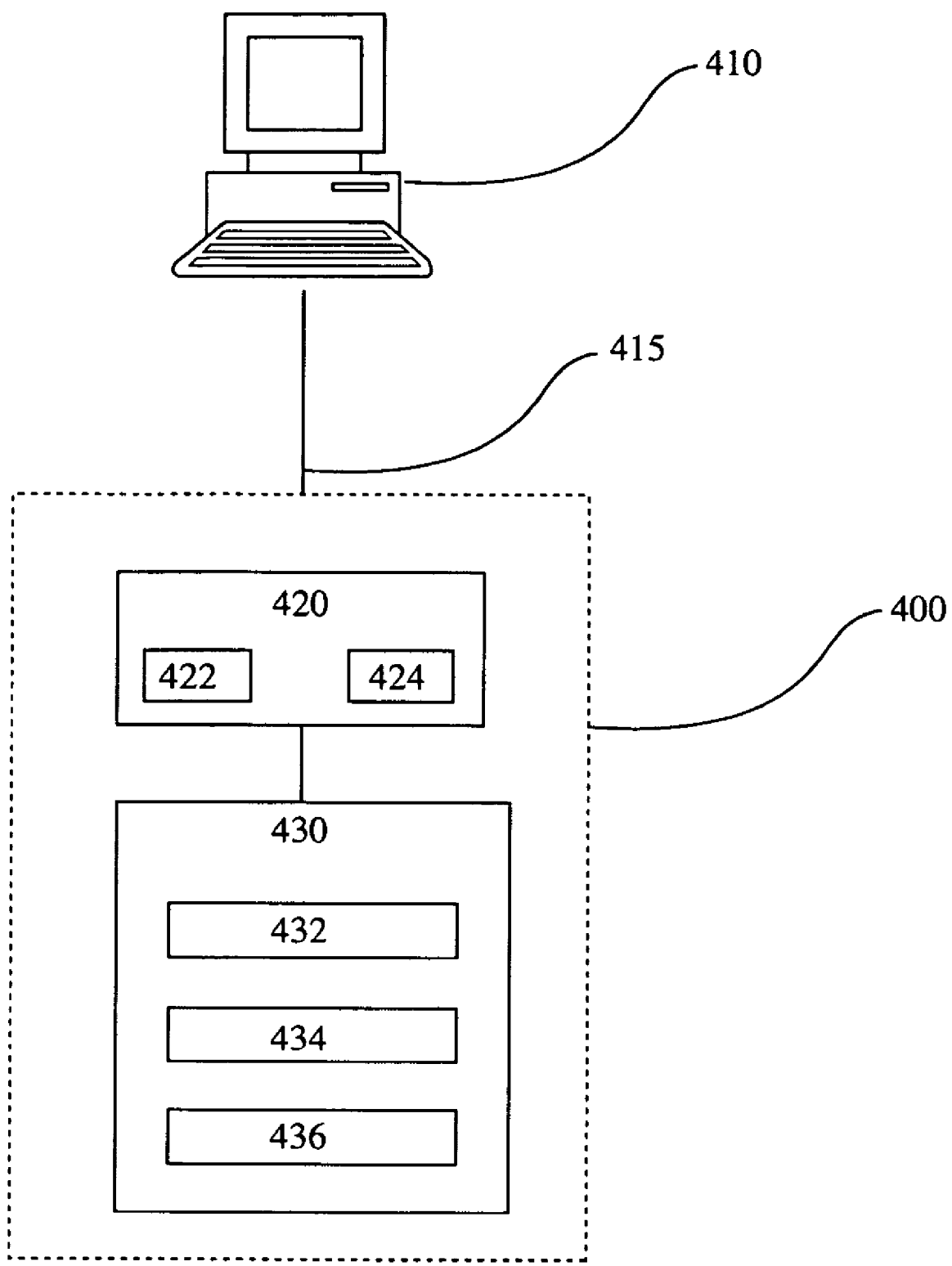
FIG. 10 illustrates a computer system.

FIG. 10 provides a view of a representative system according to an embodiment of the subject invention. In FIG. 10, system 400 includes communications module 420 and processing module 430, where each module may be present on the same or different platforms, e.g., servers, as described above. The communications module includes the input manager 422 and output manager 424 functional elements.

Input manager 422 receives information (e.g., grouping information or information on target abundance), e.g., request information, from a user e.g., over the Internet. Input manager 422 processes and forwards this information to the processing module 430. These functions are performed using any convenient technique. Another of the functional elements of communications module 420 is output manager 424. Output manager 424 provides information assembled by processing module, e.g., array layout and/or probe related content, to a user, e.g., over the Internet, also in accordance with those known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources.

The communications module 420 may be operatively connected to a user computer 410, which provides a vehicle for a user to interact with the system 400. User computer 410, shown in FIG. 10, may be a computing device specially designed and configured to support and execute any of a multitude of different applications. Computer 410 also may be any of a variety of types of general-purpose computers such as a personal computer, network server, workstation, or other computer platform now or later developed. Computer 410 may include known components such as a processor, an operating system, a graphical user interface (GUI) controller, a system memory, memory storage devices, and input-output controllers.

During use, a user employs the user computer to enter probe information into and retrieve information from the system. As shown in FIG. 10, computer 410 is coupled via network cable 415 to the system 400. Additional computers of other users in a local or wide-area network including an Intranet, the Internet, or any other network may also be coupled to system 400 via cable 415. It will be understood that cable 415 is merely representative of any type of network connectivity, which may involve cables, transmitters, relay stations, network servers, wireless communication devices, and many other components not shown suitable for the purpose. Via user computer 410, a user may operate a web browser served by a user-side Internet client to communicate via Internet with system 400. System 400 may similarly be in communication over Internet with other users and/or networks of users, as desired.

Figure 11:
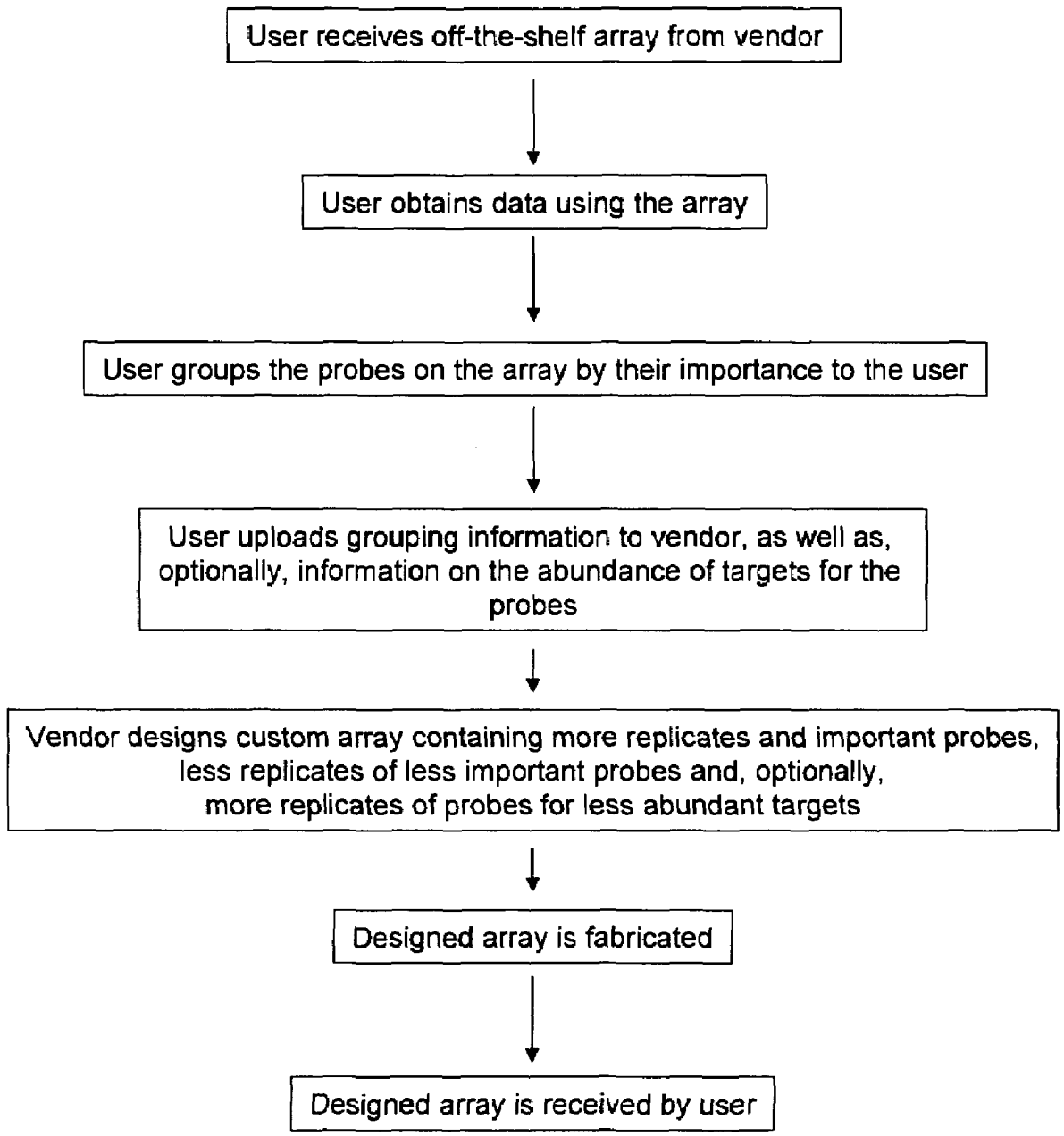
FIG. 11 is a flow chart illustrating one embodiment.

One exemplary embodiment of the instant method is set forth in FIG. 11.

In certain embodiments, a subject array may be employed to in an array-based assay, a user may receive more reliable and more accurate data from those probes that are most important to the user (i.e., the probes that are higher ranked). The data produced using a subject array may be more accurate and reliable because more replicates of each probe are available and, as such, more data points will be available for each of the "important" targets in a sample. For example, the greater the number of probe replicates are on an array, the more accurately the signal and the background for that probe may be calculated. Further, since the higher ranked probes are replicated in greater number than lower ranked probes, in certain embodiments there may be less chance of producing data that has been made unreliable because of an error or accident (e.g., an error in the fabrication or processing of the array, or a dust particle or the like).

In one embodiment, a subject array contains more features, particularly features that contain higher-ranked probes or probes for low abundance targets, that provide statistically significant signals (i.e., a signal that can be detected above noise), that are not outlier signals (i.e., signals that are statistically improbable, e.g., greater than two deviations away from the mean signal).

Methods of Producing a Biopolymeric Array

As summarized above, the subject invention includes methods of preparing biopolymeric arrays. More specifically, the subject invention provides methods of preparing biopolymeric arrays that take into account the at least suspected abundance or amount of a particular target present or suspected of being present in a sample in the design of the array. Accordingly, an array is prepared or "customized" with respect to the at least suspected (i.e., known or anticipated) abundance level of at least one target by modulating one or more parameters of an array, e.g., the number of copies of a probe for a given target, probe density, feature density, etc., based upon a target's at least suspected abundance level. In this manner, the signal obtained from the binding of the target to the respective copies of the probe may be customized or tailored to the amount of target present or suspected of being present in the sample. Accordingly, in using these customized arrays, signal may be obtained that is appropriate or commensurate with limitations of the system, e.g., with respect to noise, detection limit, etc.

It should be noted that the term "signal" is employed in the following discussion to indicate the data collected from features of a molecular array by a particular type of analysis. For example, if molecules binding to features are labeled with chromophores, and optical scans at red and green wavelengths of light are used to extract data from the molecular array, then the data collected during the optical scan at the green wavelength may be considered to be the green signal and data collected during the optical scan at the red wavelength may be considered to be the red signal. Signals of additional colors may be collected using additional dye sets. The practical limit to the number of types of signals, or colors, that may be collected is the number of emission spectra that can be independently observed. Using existing technologies, as many as twelve emission spectra may be independently observed. By using combinations of narrow band dyes, such as quantum dots, greater than twelve emission spectra may possibly be independently observed. Another type of signal may be collected by radiometric analysis of the molecular array for localized emission of one type of radiation with minimum energy levels for detection.

The term "signal" is also used to refer to data extracted from a particular feature using a particular type of analysis. It will be clear, from the context in which the term "signal" is used, below, whether "signal" refers to a cumulative set of data collected from an array via a particular type of analysis or to data collected from a particular feature of a molecular array via a particular type of analysis.

As noted above and which will be described in greater detail below, the arrays of the subject invention, i.e., arrays designed with respect to the amount of target present or suspected of being present in a sample are, in the broadest sense, arrays of polymeric or biopolymeric ligands or molecules, i.e., binding agents or probes, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. As described in greater detail below, the biopolymeric arrays of the subject invention may be employed in array assays, e.g., hybridization assays, in which the arrays are contacted with a sample containing, or suspected of containing, one or more targets of interest. Once contacted, and further processed if required, any probe/target binding complexes present on the array may be detected to provide information about the presence of the one or more targets in the sample. Because the arrays produced in accordance with the subject invention have been designed with regards to the amount of target specifically for the one or more samples with which it is to be used, the level of signal obtained from the probe/target complexes is appropriate or sufficient, if not optimal, in regards to the signal to noise ratio and/or detection limits, and the like, of the array system such that meaningful data may be obtained regardless of the amount of target in the sample.

For example, the subject methods may be employed to produce biopolymeric arrays that may be effectively used with low, including very low abundance targets, as well as high and very high abundance targets. In further describing the subject invention, unless indicated otherwise, the term "very low abundance" is meant to specify target present, or suspected of being present, in a sample in an amount that ranges from about 0.0001 pM to about 0.0010 pM, the term "low abundance" is meant to specify target present, or suspected of being present, in a sample in an amount that ranges from about 0.0010 pM to about 0.0100 pM, the term "high abundance" is meant to specify target present, or suspected of being present, in a sample in an amount that ranges from about 1 pM to about 10 pM, the term "very high abundance" is meant to specify target present, or suspected of being present, in a sample in an amount greater than about 10 pM, the term "average abundance" is meant to specify target present, or suspected of being present, in a sample in an amount that ranges from about 0.01 pM to about 1 pM.

Target Abundance

As noted above, the abundance of one or more targets present or suspected of being present in a sample is factored into the design of the array such that one or more design parameters are based in whole or in part on target abundance. Accordingly, the target abundance is characterized in some manner at some point prior to preparing the array. This characterization provides information or inputs used to design the array. More specifically, the sample is characterized at least in regards to the abundance or amount (herein used interchangeably) of a particular target in, or suspected of being in, the sample. The term "sample" as used herein relates to a material or mixture of materials, typically, although not necessarily, in fluid form, containing or suspected of containing one or more components (targets) of interest. For example, a sample may be any type of sample, whether: a trial sample; reference sample; a combination of the foregoing; or a known mixture of polynucleotides, proteins, polysaccharides and the like (in which case the arrays may be composed of features carrying unknown sequences to be evaluated). The abundance of one or more targets may be determined using any convenient protocol or analysis technique, including speculation.

Depending on the target, determining the abundance of a target may be qualitative and/or quantitative. For example, such a determination may be highly accurate and/or quantitative, or may not be so highly accurate and may include estimating or even guessing the amount of target. Accordingly, target abundance determinations are broadly defined to include any method or process for determining or evaluating, i.e., assessing or measuring, or otherwise arriving at a qualitative and/or quantitative determination of target abundance in, or suspected of being in, a sample. As such, by determining is meant to include qualitative and quantitative determinations including a determination that the abundance of a given target is unknown. The abundance of a target in a sample may be determined empirically (i.e., determined by experiment or observation) or may be determined from theory, e.g., solely or in part from theory or prior knowledge.

Qualitative and/or quantitative determinations may be made. For example, qualitative determinations may include more generalized determinations such as the determination of a particular level of a target into one of a plurality of categories, classes or groups of abundance. For example, categories may range from a very small amount of target to a very large amount of target. For example, a determination may result in categorizing the amount into one of the following or analogous categories: very low abundance, low abundance, average, high abundance, very high abundance or unknown. Other categories may be employed as well such that a given target may not be assigned an exact number relating to its concentration in a sample, but may be assigned to a category, group or class.

Analytical protocols may be employed. For example, in certain embodiments the abundance of a target may be determined by contacting the sample containing or suspected of containing the one or more targets of interest with a first or test array and performing a test array assay. Information obtained from performing a test array assay may then be used to determine target abundance such that the results of the test assay may provide information about the abundance of a target in the sample which may be used in the design of the array. For example, if signal for a given target obtained from the test array is a very low signal, the target may be determined to be in low or very low abundance in the sample. For example, a test array may be a genome-wide array directed to a particular species. Other processes of qualitative and/or quantitative analysis that may be employed to determine the abundance of a target in a include, but are not limited to, spectroscopic techniques, mass spectrometry, e.g., MALDI-ToF mass spectrometry, polarography, chromatography, electrophoretic techniques such as 2-D electrophoresis, spectroscopy, activation analysis, and the like.

As noted above, in certain embodiments the abundance of a target may be determined based in whole or in part on prior knowledge and include educated guesses, speculation, etc. As noted above, in certain embodiments the abundance of a target may be determined to be unknown.

Determining Appropriate Array Parameters Based on Target Abundance

Once the abundance of one or more targets is determined, certain parameters of the array may be selected with respect to the abundance such that an array may be customized or tailored based on target abundance. Information or inputs for selecting appropriate array parameters based on the at least suspected target abundance may be obtained as described above, and/or from information obtained from previously designed arrays, e.g., when employed in array assays, e.g., array design may be an iterative process. For example, the subject methods may include obtaining information from previously prepared arrays, whether prepared in accordance to the subject methods or another method, and using that information in future array designs. For example, an array design may be iterated one or more times, each time changing one or more of the array design parameters, e.g., based on previous array assay results obtained by using previously prepared arrays in array assays, until the signals obtained from an array meets predetermined criteria such as design specifications and the like.

A variety of different parameters may be tailored with respect to target abundance in or suspected of being in a sample, including, but not limited to, the number of copies of a given probe for a given target, the number of replicates of a given feature for a given target, the density of probe copies in a given feature, i.e., the probe density, the feature density, and the like. While parameters such as probe copy number, feature number, probe density and feature density are described as exemplary array parameters that may be tailored with respect to target abundance, such is for exemplary purposes only and is in no way intended to limit the scope of the invention as it will be apparent to those of skill in the art that other array parameters may also be tailored with respect to target abundance. In further describing the subject invention, exemplary array parameters that may be customized with respect to target abundance are now described in greater detail.

Embodiments include preparing a biopolymeric array by determining the at least suspected relative abundance of targets in a sample type for which the array is designed to be used, and immobilizing populations of different probes for respective targets at relative numbers or amounts that are dependent upon the at least suspected relative abundance of the targets. Embodiments include preparing a biopolymeric array by determining the at least suspected the relative abundance of targets in a sample type for which the array is designed to be used, and immobilizing populations of different probes for respective targets at relative total feature areas which are dependent upon the at least suspected relative abundance of the targets, e.g., using different numbers of features of the same size; the same number of features of different sizes, combinations thereof, and the like.

Probe Copy Number

As described above, embodiments include customizing probe copy number to target abundance. Accordingly, embodiments of the subject methods include determining the copy number of a given probe for a given target based at least in part on the abundance of the target in or suspected of being in a sample. As will be described in greater detail below, the appropriate number of probe copies may then be immobilized on a substrate to provide a biopolymeric array.

As noted above, in certain embodiments information related to the abundance of one or more targets present or suspected of being present in a sample is employed in the design of the array, i.e., is used as an input in the array design, and more specifically is used to determine the number of copies of a given probe directed to a given target. In this manner, a given probe may be customized or designed with respect to probe copy number to provide a particular signal level relating to a specific target. This may be desired in instances where the abundance of a target is low or high, e.g., relative to noise, detection limit, and the like, and in such instances poor or less than optimum array assay results may be obtained due to the signal to noise ratio if the abundance of the target were not taken into account in the array design.

For example, in performing an array assay with a target determined to be in low or very low abundance, the signal may be at such a low level that the signal to noise ratio may be too low to provide meaningful array assay results, e.g., too low to delineate or distinguish signal from system noise if the array were not designed to account for the low or very low amount of target. Similarly, in performing an array assay with a target determined to be in high or very high abundance, the signal may be at such a high level that the signal may be too great to provide meaningful array assay results if the array were not designed to account for the high or very high amount of target.

The number of copies of given probe may be determined using any convenient protocol. In certain embodiments, an algorithm is employed, e.g., in conjunction with a computational analysis system, to identify the copy number (and/or feature number and/or copy density as will be described in greater detail below) where target abundance is an input in the algorithm. Any convenient algorithm or process capable of performing the above function may be employed.

For example, the inventors of the subject invention have realized that, all other things being equal and assuming constant probe density in the linear range of binding, the signal to noise ratio of a target will scale proportionally to the square root of the area on the array containing probes that bind to that target. This analysis is based on the observation that for a normally distributed (i.e., Gaussian) set of signals and noise, the standard deviation of the mean of the measurements taken varies proportionally to the inverse of the square root of the number of data points. Therefore, the inventors have realized that if, e.g., twice the number of copies of a given probe (or twice the number of replicate features of a given probe, etc.) are provided on an array, twice as many data points or pixels or signal for a particular target may be obtained. In certain embodiments, the number of probe copies (and/or feature number, etc.) is determined at least in part on this observation.

In certain embodiments, the number of copies of a probe may be proportional to the square root of the expected signal for that target, where the level of signal expected is based on abundance of the target. For example, a target that is expected to be half as bright as an average signal for the array system, may have four times as many copies of a probe for that target as the target of average abundance (i.e., one that would provide an average expected signal). Such may be the case for target determined or even suspected of being present in a low concentration in the sample or for a target of unknown abundance. Since these "scarce" targets will tend to have low signal and thus low signal to noise (relative to an average target), increasing the number of copies will improve the signal to noise ratio. Accordingly, in certain embodiments, an average copy number corresponding to probes for a target of average abundance (i.e., present in an amount ranging from about 0.01 pM to about 1 pM which may have an expected average scanner signal level ranging from about 50 counts to about 5,000 counts) may be about $6 \times 10^8$ probes/feature. Accordingly, for low or very low abundance targets, the copy number may be more than the copy number of an average abundance target, e.g., may be about 0.001% more to about 100% or more, e.g., may be about two times, about three times. For example, in certain embodiments the average probe copy number for a target at least suspected of being present in a sample in very low abundance may range from about $6 \times 10^6$ probes/feature to about $6 \times 10^{12}$ probes/feature and the average probe copy number for a target at least suspected of being present in a sample in low abundance may range from about $6 \times 10^5$ probes/feature to about $6 \times 10^{11}$ probes/feature. In certain embodiments the average probe copy number for a target at least suspected of being present in a sample in an average amount may range from about $6 \times 10^5$ probes/feature to about $6 \times 10^{11}$ probes/feature.

In certain instances, a target may be in, or suspected of being in, high or very high abundance. For targets of high or very high abundance, signal obtained therefrom may be too high for the detection system, thus preventing meaningful results from being obtained. For example, there may a chance that the pixels for features to such high abundance targets may become saturated (or the upper end of the dynamic range of the system may be exceeded either by exceeding the scanner's saturation limit or saturating the number of probe molecules for the target). In such instances, the number of probe copies may be decreased proportionally to the expected signal. Such embodiments would thus dilute the signal over more pixels which in turn may reduce the signal to a level below the saturation level. For example, analogous to that described above for a low or very low abundance target, a target that is expected to be twice as bright as an average signal for the array system, may have half as many copies of a probe for that target as the target of average abundance (i.e., one that would provide an average expected signal). Such may be the case for target determined or even suspected of being present in a high concentration in the sample or for a target of unknown abundance. Since these high or very high abundance targets will tend to have high signal, decreasing the number of copies may improve the detection of thereof. Accordingly, in certain embodiments, for high or very high abundance targets, the copy number may be less, e.g., a fraction, of the average copy number as described above, e.g., about 9/10, e.g., about 4/5, about 3/4, about 1/2, about 1/4, or even about 1/5 or less the average copy number. For example, in certain embodiments the average probe copy number for a target at least suspected of being present in a sample in very high abundance may range from about $6 \times 10^4$ probes/feature to about $6 \times 10^{10}$ probes/feature and the average probe copy number for a target at least suspected of being present in a sample in high abundance may be chosen to provide a scanner signal level of about 5,000 counts, e.g., the average probe copy number for a high abundance target may range from about $6 \times 10^4$ probes/feature to about $6 \times 10^{10}$ probes/feature. In certain embodiments the average probe copy number for a target at least suspected of being present in a sample in an average amount may range from about $6 \times 10^5$ probes/feature to about $6 \times 10^{11}$ probes/feature.

The number of copies of a given probe for a given target in a given feature may thus be chosen at least in part on the amount of target directed for that probe that is present or suspected of being present in the sample.

Feature Replicates

As noted above, in addition to determining the number of copies of a particular probe for a particular target based at least in part on the amount of target present or suspected of being present in a sample, other relevant parameters of the probes may be determined based at least in part on the amount of target present or suspected pf being present in a sample. For example, in addition or instead of tailoring the number of copies of a given probe for a given target to target abundance, array features may be tailored with respect to the number of features of a given polymeric probe, i.e., the number of replicate features. By replicate feature is meant features made of copies to the same probe. In certain embodiments, methods include determining the appropriate probe copy number— either total probe copy number (i.e., spread amongst one or more features such s replicate features) or probe copy number per feature, and then determining the number of features, if more than one, that will include the probe copy number.

For example, in tailoring the copy number of a particular probe for a given target, the copies of a given probe may be immobilized onto a substrate surface in a number of different formats, depending on the amount of target present or suspected of being present, to provide the best array assay results using the system that includes the produced array and sample. For example, all the copies of particular probe may be immobilized as one feature or spot on the array substrate surface or may be immobilized in two or more features, i.e., replicate features. More specifically, embodiments include features present in multiple copies, e.g., in duplicate, triplicate, quadruplicate, quintuple, sextuple, etc., where such is determined at least in part on the amount of target present or suspected of being present in a sample contact with the probe copies. Determining the appropriate number of replicate features may be accomplished in any convenient manner, including methods analogous to those described above for determining a number of copies of a probe.

For example, in instances where a target is a low or very low abundance target, it may be determined that the entire population of probe copies for such a target be immobilized as a single feature. Likewise, in instances where a target is a high or very high abundance target, it may be determined that the entire population of probe copies for such a target be immobilized as more than one feature to spread out or dilute the signal over multiple features.

Accordingly, a population of copies of a given probe may be arranged in one or more features. Whether copies of a given probe are present in one or more features may be dependant at least in part on the abundance of the target in the sample where the number of features made-up of a number of copies of a particular probe may range from about 1 to about 100 or more. For example, high to average signal level features may have features present in replicates that range from about 1 to about 5 replicates and low to very low signal level features may have replicates that ranges from about 1 to about 100 replicates or more.

Feature Size

The size of the features of an array may also be chosen with respect to the abundance of a target. For example, low or very low abundance targets may have features that are smaller in size with respect to at least one dimension than average, high or very high abundance targets. In general, embodiments may have features with widths (that is, diameter, for a round spot) in the range from about 10 µm to about 1.0 cm. In certain embodiments, each feature may have a width in the range from about 1.0 µm to about 1.0 mm, usually from about 5.0 µm to about 500 µm and more usually from about 10 µm to about 200 µm, e.g., from about 50 µm to about 150 µm. Non-round features may have area ranges equivalent to that of circular features with the foregoing width (diameter) ranges. In certain embodiments, methods include determining the appropriate probe copy number—either total probe copy number (i.e., spread amongst one or more features such s replicate features) or probe copy number per feature, and then determining feature size.

In certain embodiments, features to low or very low abundance targets may have larger sizes relative to features for average, high or very high abundance targets. For example, where the amount of target in or suspected of being in a sample is a low or very low abundant target, a round feature to such a target may have dimensions corresponding to this abundance level, e.g., may have a width that ranges from about 100 µm to about 1 mm.

In certain embodiments, features to high or very high abundance targets may have smaller sizes relative to features for average, low or very low abundance targets. For example, where the amount of target in or suspected of being in a high or very high abundant target, a round feature to such a target may have dimensions corresponding to this abundance level, e.g., may have a width that ranges from about 5 µm to about 100 µm.

Probe Density

The density of a feature, i.e., the density of copies of a given probe that makeup a feature is also of importance to the array design. Accordingly, certain embodiments include customizing feature probe density based at least in part on target abundance. For example, in certain embodiments features to low or very low abundance targets may have higher probe densities relative to average or high or very high abundance targets. Likewise, in certain embodiments features to high or very high abundance targets may have lower densities relative to features for average, low or very low abundance targets. In certain embodiments, methods include determining the appropriate probe copy number—either total probe copy number (i.e., spread amongst one or more features such as replicate features) or probe copy number per feature, and then determining feature probe density.

In general, feature probe densities may range from about 0.001 pmoles/mm$^2$ to about 10 pmoles/mm$^2$ depending on the at least suspected level of target in a sample for which the probes are designed to bind, where in certain embodiments the densities of probe molecules in a given feature may be more than about 10 pmoles/mm$^2$ or less than about 0.001 pmoles/mm$^2$.

For example, embodiments may include features to low or very low abundance targets. Such features may have probe densities corresponding to this abundance level, e.g., may have probe densities that may fall within the mid to higher ends of the ranges described above. For example, probe densities for such features may ranges from about 0.1 pmoles/mm$^2$ to about 10 pmoles/mm$^2$. Embodiments may also include features to high or very high abundance targets. Such features may have probe densities corresponding to this abundance level, e.g., may have probe densities that may fall within the mid to lower ends of the ranges described above. For example, densities for such features may range from about 0.1 pmoles/mm$^2$ to about 0.001 pmoles/mm$^2$.

As noted above, certain array embodiments include a plurality of features for the same or different target, where some or all of the features may differ in one or more aspects. For example, in certain embodiments copies of a given probe (i.e., exact copies of a given probe) may be immobilized in two or more features and some or all of the replicate features may differ in one or more aspects. For example, in those instances where the same probe copies are present in two or more features, some or all of the features may differ with respect to copy number and density of copies, i.e., probe densities. For example, a population made-up of a plurality of copies of a given probe may be immobilized on a substrate surface in at least a first feature and a second feature. In certain embodiments, first and second features may be the same with respect to copy number and probe density. However, in certain other embodiments first and second features may differ in copy number and/or probe density. For example, if a sample is determined to be present in an unknown amount in a sample, an array may include a variety of different features where some or all of the features may be the same or some or all may differ with respect to copy number and/or probe density.

Embodiments also include features to different targets, i.e., features that are made-up of copies of different probes, i.e., probes of different compositions. For example, a substrate may include at least a first feature of a particular number of copies of a first probe to a first target and at least a second different feature of a particular number of copies of a second probe to a second target. Accordingly, in addition to differing in the particular probe employed, first and second features may also differ with respect to probe copy number, feature number and density of copies in a feature. This may be desirable in those instances where different targets are determined to be in disparate amounts in a sample.

However, in certain embodiments, some or all of the features, whether they include copies to the same or different probe, may be the same at least with respect to copy number and/or probe density and/or feature number if features of different probe copies are present. For example, in certain embodiments at least a first set of features may be for a low or very low abundance target and a second set of features may also be for a low or very low abundance target and as such the copy number and/or probe density and/or feature number of the first and second feature sets may be analogous. Likewise, in certain embodiments at least a first set of features may be for a high or very high abundance target and a second set of features may also be for a high or very high abundance target and as such the copy number and/or probe density and/or feature number of the first and second feature sets may be analogous.

Accordingly, the number of distinct polymeric sequences, and hence spots or similar structures, present on the array may vary, where a typical array may contain more than about ten, more than about one hundred, more than about one thousand, more than about ten thousand or even more than about one hundred thousand features in an area of less than about 20 cm$^2$ or even less than about 10 cm$^2$. At least some, or all, of the features are of different compositions (for example, when any repeats of each feature composition are excluded, the remaining features may account for at least about 5%, 30% or 90% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents, but may not be present when, for example, photolithographic array fabrication process are used. It will be appreciated though, that the interfeature areas, when present, could be of various sizes and configurations. The spots or features of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like.

Figure 2:
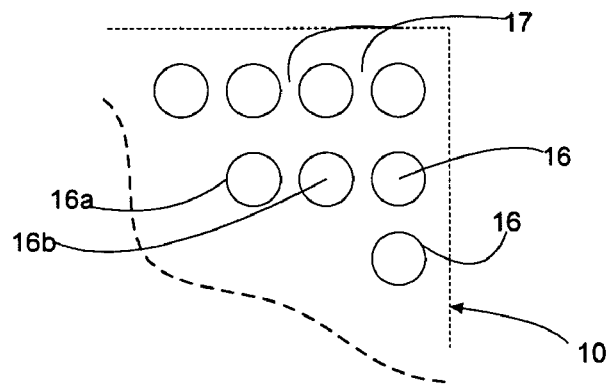
FIG. 2 is an enlarged view of a portion of FIG. 1 showing multiple ideal spots or features of an array.
Figure 3:
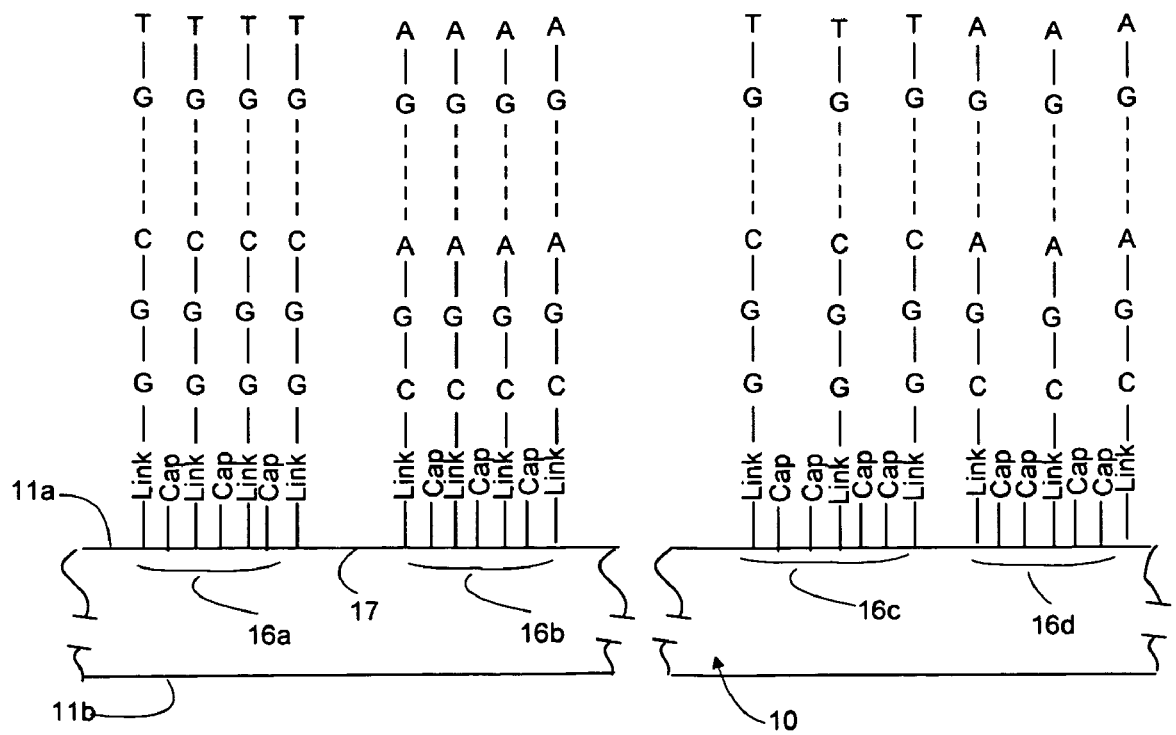
FIG. 3 is an enlarged illustration of a portion of FIG. 2.

In providing feature probe densities based at least in part on the at least suspected target abundance, one or more of the arrays may be duplicated on a surface with the same features except that features of the same composition may have different feature probe densities (and/or copy number and/or feature density and/or feature size, and the like). In one example of this, in the configuration of FIG. 1 arrays 12$a$, 12$b$ may be different arrays with at least some (or all) features of different probe composition. (It is to be understood that the description relating to probe densities with respect to FIGS. 1, 2, 3, 5 and 6 may be applied to other array parameters such as copy number and/or feature density and/or feature size, and the like.) Referring to FIGS. 1-3, array assembly 15 of the present invention may include a substrate which can be, for example, in the form of an a rigid substrate 10 (for example, a transparent non-porous material such as glass or silica) of limited length, carrying one or more arrays 12 disposed along a front surface 11$a$ of substrate 10 and separated by inter-array areas 14. Throughout this application any different members of a generic class may have the same reference number followed by different letters (for example, arrays 12$a$, 12$b$, 12$c$, and 12$d$ may generically be referenced as "arrays 12") Alternatively, substrate 10 can be flexible. Each array 12 occupies its own region on surface 11$a$ which is co-extensive with the array (hence the regions do not extend into areas 14). A back side 11$b$ of substrate 10 does not carry any arrays 12. The arrays on substrate 10 can be designed for testing against any type of sample, whether: a trial sample; reference sample; a combination of the foregoing; or a known mixture of polynucleotides, proteins, polysaccharides and the like (in which case the arrays may be composed of features carrying unknown sequences to be evaluated). While four arrays 12 are shown in FIG. 1, it will be understood that substrate 10 and the embodiments to be used with it, may use any number of desired arrays 12 such as at least one, two, five, ten, twenty, fifty, or one hundred (or even at least five hundred, one thousand, or at least three thousand). When more than one array 12 is present they may be arranged end to end along the lengthwise direction of substrate 10. Depending upon intended use, any or all of arrays 12 may be the same or different from one another and each will contain multiple spots or features 16 of biopolymers in the form of polynucleotides.

Array 12$c$ may repeat some or all of the features of array 12$a$ but at a lower feature probe density in each feature than in array 12$a$, while array 12$d$ may repeat some (or all) of the features of array 12$b$ but also at a lower feature probe density than in array 12$b$. All features within a same array may have the same feature probe density, with probes bound to surface 11$a$ through linker agents identified as "Link" in FIG. 3. A capping agent is also present on each of the features 12$a$-12$d$. Note that in this particular example all features in arrays 12$a$, 12$b$ have the same feature probe density and linker agent density while those features in arrays 12$b$, 12$c$ also have the same feature probe density and linker agent density both of which are lower than in arrays 12$a$, 12$b$. Also, the different regions occupied by arrays 12$c$, 12$d$ have a capping agent density which is lower than the capping agent density at the regions occupied by arrays 12$a$, 12$b$. The foregoing relative densities can be best seen in FIG. 3 wherein feature 16$a$ is located in array 12$a$, feature 16$b$ in array 12$b$, feature 16$c$ in array 12$c$, and feature 16$d$ in array 12$d$. Thus, features 16$a$, 16$c$ are features of a same probe composition but with different feature probe densities and different region linker agent/ capping agent densities. Similarly features 16$b$, 16$d$ are of a same probe composition but with different feature probe density and different region linker agent/capping agent densities. Such embodiments may be desirable, for example, in instances where the abundance of a target is unknown in a sample for which the array is designed to assay.

While in FIG. 1 the substrate surface has four regions (the regions occupied by arrays 12$a$, 12$b$, 12$c$, 12$d$) at which a linking agent is bound (two pairs of two regions at different densities) other configurations can be provided. For example, referring to FIG. 5 substrate 10 has two distinct regions each carrying an array 12$e$, 12$f$ which have the same array layout and probe compositions but with different densities as already described, based at least in part on the at least suspected target abundance in a sample for which the array is designed to assay. Similarly, substrate 10 in FIG. 6 has two arrays of different layout and probe compositions, with array 12$g$ being repeated as arrays 12$h$ to 12$m$ in the regions coextensive with those arrays and which have successively higher feature probe densities and region linker agent densities, and successively lower capping agent density, going from array 12$g$ to array 12$m$. Similarly, the different array 12$n$ is repeated as arrays 12$n$ to 12$t$ in the regions coextensive with those arrays and which have successively higher feature probe densities and region linker agent densities, and successively lower capping agent density, going from array 12$n$ to array 12$t$. Furthermore, regions of different linking agent density may carry parts of a single array (that is, the same array has regions of different probe feature density) with the features in one part being repeated at a different feature probe density in another part. For example, arrays 12$a$, 12$c$ could be positioned immediately adjacent each other to form a single array. This can, for example, be accomplished where there is precise control over the boundaries of the different regions with different linker agent density, such as is possible with the apparatus and methods described below in connection with FIGS. 4 and 7.

To fabricate arrays of FIGS. 1-3, 5, 6 a surface modified substrate may first be produced. Such a substrate will have the characteristics described above but with no features (thus, no probes) present in each region.

Preparing a Biopolymeric Array Based on Parameters Determined With Respect to Target Abundance Once the abundance of at least one target in the sample is determined and the appropriate array parameters such as copy number of a probe for a given target is determined, feature number of a particular probe is determined, feature replicate number, feature probe density of a particular probe is determined, feature density of a particular probe is determined, feature size, etc., at least in part based on the at least suspected abundance of a target in a sample for which the array is designed to assay, a biopolymeric array may be prepared based on this information.

In general, the one more features of probe copies are designed with respect to target abundance and produced or immobilized on a substrate surface to provide a biopolymeric array. Arrays of the subject invention typically include at least two distinct polymers (i.e., two distinct probes), e.g., that differ by monomeric sequence, attached to different and known locations on the array substrate surface. As noted above, each distinct polymeric sequence of the array is typically present as a composition of multiple copies of the polymer on a substrate surface, e.g., as a spot or feature on the surface of the substrate, where the number of copies and/or number of features and/or feature density with respect to a given probe is determined at least in part according to the abundance of the target.

The arrays of the subject invention may be produced using any convenient protocol. Various methods for forming arrays from pre-formed probes, or methods for generating the array using synthesis techniques to produce the probes in situ, including known light directed synthesis processes, may be employed and are generally known in the art (see, for example, U.S. Pat. Nos. 6,180,351; 6,242,266; 6,306,599 and 6,420,180, the disclosures of which are incorporated herein by reference). For example, probes may either be synthesized directly on the array solid support or substrate or attached to the substrate after they are made. Arrays may be fabricated using drop deposition from pulse jets of either probe precursor units, e.g., polynucleotide precursor units (such as monomers), in the case of in situ fabrication, or the previously obtained probe, e.g., previously obtained polynucleotide. Other drop deposition methods may be used for fabrication. Also, instead of drop deposition methods, photolithographic array fabrication methods may be used. As mentioned above, interfeature areas need not be present, particularly when the arrays are made by photolithographic methods as described in those patents. Accordingly, as described above, the probes may be synthesized directly on a substrate, or pre-made probes may be attached to the substrate.

Immobilization of a probe to a suitable substrate may be performed using conventional techniques. See, e.g., Letsinger et al. (1975) Nucl. Acids Res. 2:773-786; Pease, A. C. et al., Proc. Nat. Acad. Sci. USA, 1994, 91:5022-5026, and Oligonucleotide Synthesis, a Practical Approach," Gait, M. J. (ed.), Oxford, England: IRL Press (1984). The surface of a substrate may be treated with an organosilane coupling agent to functionalize the surface. See, e.g., Arkins, ASilane Coupling Agent Chemistry," Petrarch Systems Register and Review, Eds. Anderson et al. (1987) and U.S. Pat. No. 6,258, 454.

Any given substrate may carry one, two, four or more arrays disposed on a surface of the substrate. Depending upon the use, any or all of the arrays may be the same or different from one another and each may contain multiple spots or features as noted above. For example, a plurality of arrays may be stably associated with one substrate, where the arrays are spatially separated from some or all of the other arrays associated with the substrate.

The probes may be immobilized on surfaces of any of a variety of different substrates, including both flexible and rigid substrates. Typically, the materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example, a slide or plate configuration, such as a rectangular or square disc. In many embodiments, the substrate will be shaped generally as a rectangular solid, having a length in the range of about 4 mm to 200 mm, usually about 4 mm to 150 mm, more usually about 4 mm to 125 mm; a width in the range of about 4 mm to 200 mm, usually about 4 mm to 120 mm, and more usually about 4 mm to about 80 mm; and a thickness in the range of about 0.01 mm to about 5 mm, usually from about 0.1 mm to about 2 mm and more usually from about 0.2 mm to about 1 mm. However, larger or smaller substrates may be and can be used. Substrates of other configurations and equivalent areas may be employed. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fuse silica; silicon, plastics (for example polytetraflouroethylene, polypropylene, polystyrene, polycarbonate, and blends thereof, and the like); metals (for example, gold, platinum, and the like).

The substrate surface onto which the probes are immobilized may be smooth or substantially planar, or have irregularities, such as depressions or elevations. The substrate surface may be modified with one or more different layers of compounds that serve to modify the properties of the surface in a desirable manner. Such modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyetheyleneamines, polyarylene sulfides, polysiloxanes, polyimides, polyacetates, and the like, where the polymers may be hetero- or homopolymeric, and may or may not have separate functional moieties attached thereto (for example, conjugated).

Methods of Making Surface Modified Substrates and Arrays

As noted above, the subject invention also include methods of making surface modified substrates and arrays, where the surface modified substrates and arrays are tailored at least in part on the at least anticipated abundance of a target in a sample for which the array is designed to assay. One way of producing surface modified substrates as described above is to first modify front surface 11a of substrate 10 by depositing drops containing a linking agent (such as a linking agent and a suitable solvent) onto the surface, so that the linking agent will bind to the substrate surface. Additionally, drops may be deposited which include a capping agent onto the surface, which drops may be the same or different from those containing the linking agent. When the same drops are used those with a higher concentration of linking agent will generally contain a lower concentration of capping agent. In either event the deposited drops containing the linking agent or the capping agent are of such a size, and are sufficiently close together, so that together such drops cover a desired region over the surface. For example, at least 10, at least 100, at least 200, or at least 1000 drops deposited at different locations on the surface will together cover a region on surface 11a. By covering a "region" on the surface does not mean that the drops must simultaneously be in liquid form, but in fact some may have already dried. Instead they need only be of sufficient size and sufficiently close together such that the total region occupied by them (dry or not) is continuous. Drops size and spacing can be adjusted by known methods particularly when pulse jets are used to deposit the drops.

The linking agent and capping agent will bind to the different regions to produce a substrate surface having both linking agent and capping agent bound to the different regions with a lower density of capping agent at a region which has a higher density of linking agent. The different regions could be coextensive with the different arrays described above. For example, the there could be four regions each coextensive with arrays 12a, 12b, 12c, 12d in FIG. 1, with the regions for arrays 12a, 12b having a same region linking agent density and those regions for arrays 12c, 12d also having a same region linking agent density, but with regions for arrays 12a, 12b having a higher region linking agent density than the regions for arrays 12c, 12d. However, this need not necessarily be the case. For example, in the array assembly of FIG. 1 one half of surface 11a (that half carrying arrays 12a, 12b) could be produced with a higher linking agent density, while the other half (carrying arrays 12c, 12d) could be produced with a lower linking agent density. Similarly, in FIG. 6 rather than each region being coextensive with an individual array therein, each region could be formed as a stripe across the surface which will encompass two arrays of the same feature probe density (for example, one stripe will encompass arrays 12g, 12n, a next stripe will encompass arrays 12h, 12o and so on with linker agent density increasing in successive stripes moving from left to right in FIG. 6).

Figure 4:
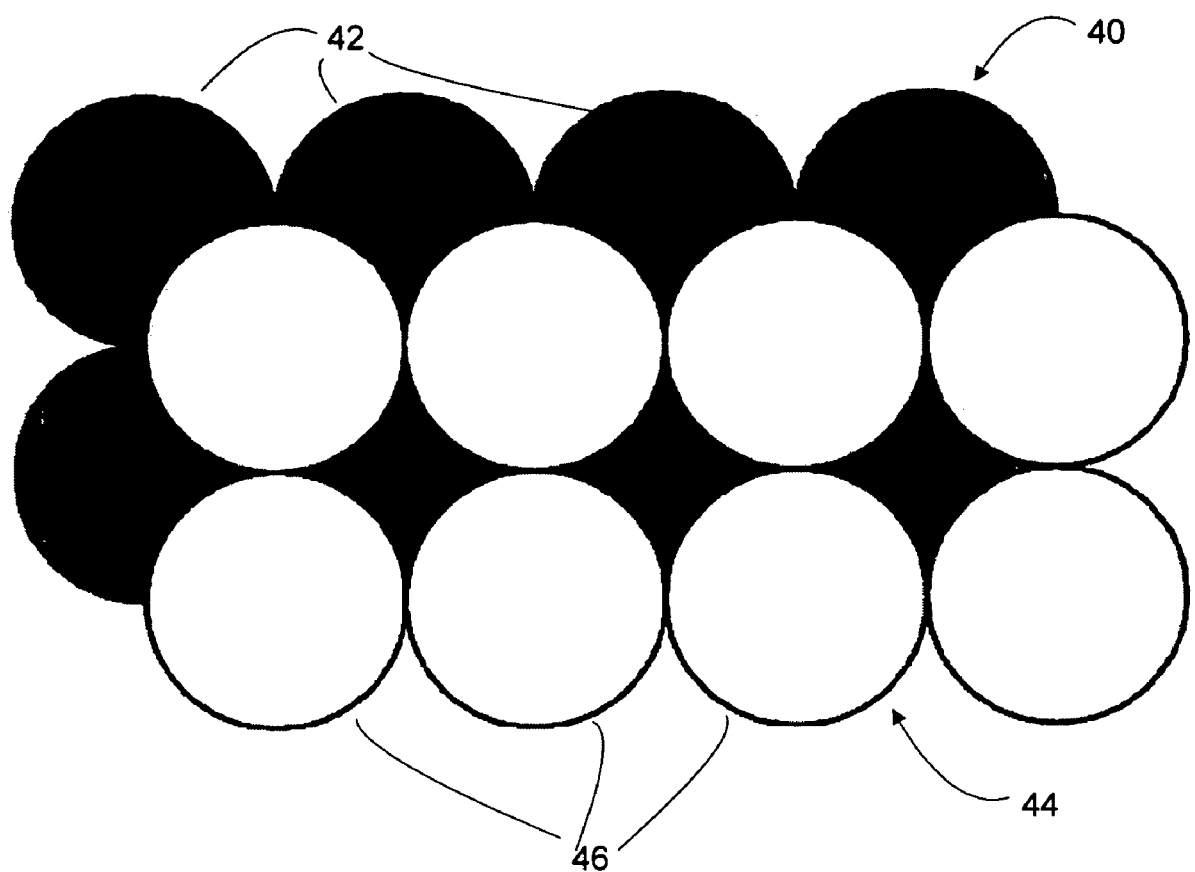
FIG. 4 illustrates a method of depositing drops of a surface linking agent, additional agent such as surface energy modifier, or solvent, to produce a region of a desired linking agent and capping agent density.

One procedure for producing a surface of desired linker agent and capping agent densities, is illustrated in FIG. 4. In FIG. 4 one or more heads such as head 210 (see below) makes one pass to deposit drops of a liquid (for example, solvent, linking agent, or additional agent). In FIG. 4 eight drops 42 have been deposited to form one continuous layer 40. To ensure no gaps are present the head makes another pass to deposit the same liquid in eight drops 46 to form another continuous layer 44. Thus drops 42 and 46 together cover a continuous area (the union of the areas represented by layers 40 and 44) with no gaps. In practice, the continuous area may be the entire area of a substrate surface, or at least 50%, 25%, 10% or 5% of such area. Regardless of the foregoing, the continuous area will normally cover at least the continuous area occupied by multiple adjacent features of an array 12 to be fabricated on the substrate or the entire continuous area occupied by an array 12, with different continuous areas for different arrays 12. Alternatively, the continuous area may be at least $0.1$ cm$^2$, at least $0.2$ cm$^2$, or at least $0.5$ cm$^2$ or $1$ cm$^2$.

One way to produce a surface modified substrate by a method of the present invention, drops which include a solvent may be first deposited onto the substrate surface to cover a continuous area using the method as described in connection with FIG. 4. Drops which include the linking agent may then be deposited in the manner described in connection with FIG. 4 also to cover a same continuous area as the solvent deposited drops. These drops may include a capping agent or such capping agent may be in drops deposited later to cover a same continuous area as covered by the drops containing the linking agent. In either event, the linking agent binds to the surface so that probe or probe precursors subsequently deposited in further drops at aim feature locations for an array 12 will bind to the linking agent but not to the capping agent. However, further processing of a functional group on a linking agent may be necessary for such binding to occur.

As to a suitable capping agents this may particularly be any of the first silanes as set out in detail U.S. Pat. No. 6,444,268, while the linking agent may be any of the second silanes therein and the solvent may be as described in that patent also (for example, toluene). As already mentioned, that patent is incorporated herein by reference, including for example the details of the first and second silanes and solvents used therein. In one embodiment as described in the foregoing patent the first silane has the formula $R^1$—Si($R^L R^x R^y$) and the second silane has the formula $R^2$—(L)$_n$—Si($R^L R^x R^y$) so that binding to the surface provides —Si—$R^1$ groups and —Si—(L)$_n$—$R^2$ groups thereon, wherein the $R^L$, moieties, which may be the same or different, are leaving groups, the $R^x$ and $R^y$ are independently lower alkyl or leaving groups, $R^1$ is a chemically inert moiety that upon binding to the substrate surface lowers the surface energy thereof, n is 0 or 1, L is a linking group, and $R^2$ is a functional group enabling covalent binding of a molecular moiety or a modifiable group that may be converted to such a functional group. Leaving groups in the foregoing may include halogen and alkoxy. Both the first and second silanes bind to the surface through reactive hydrophilic moieties thereon, which are selected from the group consisting of hydroxyl, carboxyl, thiol, amino, and combinations thereof. The foregoing terms and other emobidments of the first and second silanes are further defined in the foregoing patent. However, in this method, unlike in the foregoing patent, drops of the solvent (for example, toluene) may be dispensed onto the surface 11a so that together they cover a continuous area with no gaps, as described in connection with FIG. 4. This may be followed by depositing drops of the second silane to cover the same continuous area. The drops containing the second silane may also contain the first silane. The substrate 10 may then be physically and chemically processed as described in detail in U.S. Pat. No. 6,444,268. If the second silane was not present in the drops containing the first silane, then drops containing the second silane may be deposited onto the substrate surface to cover the same continuous area at this point, and allowed to react therewith for about 30 minutes. In either situation, the relative amounts of the first and second silanes can be adjusted to control surface energy as also described in detail in U.S. Pat. No. 6,444,268.

In one example, two printheads 210 may be used, the first to deposit a toluene/water solvent mixture, and a second to deposit the pure or diluted mixture of the first and second silanes. Due to the low surface tension of toluene, only a few passes of the printheads are needed to obtain complete coverage of a front surface 11a of substrate 10. In particular, drops of the solvent and silane mixture are each applied in a pattern similar to that shown in FIG. 4. A total volume of 5 ml will form a 200 Φm thick continuous layer of toluene/water solution or silane solution on a 6 inch by 6 inch substrate, and at the concentrations described in the foregoing patent the silane containing layer will contain enough silane to completely react with all sites on the wetted substrate surface. The substrate is then placed in a holding chamber for about 20 minutes to allow the reaction (covalent binding of the first and second silanes with reactive hydroxyls on the substrate surface) to go to completion.

In a second example, three printheads 210 may be used. One is used for depositing drops of the toluene/water mixture, and another one each for pure or diluted first and second silanes. This example is the same as in the first example, except here drops containing the first and second silanes are separately deposited. In particular, after deposition of the toluene/water solvent containing drops, drops containing the second silane are then deposited to provide a continuous layer over the substrate front surface (again, about 5 ml can be used). The concentration of the second silane is adjusted to react with only a fraction of the total sites available for reaction on the front surface. After 20 minutes waiting time at room temperature, the substrate is rinsed in toluene and dried. At this point, the linking agent will be linked to a portion of the sites on the front surface. Surface functionalization is then completed by depositing drops of toluene/water then drops containing the first silane, with the first silane concentration adjusted in excess to react with 1000 times the total sites available on the front surface of the substrate. After application the substrate is placed in a holding chamber for about 20 minutes to allow the reaction (covalent binding of the first silane to the reactive hydroxyls on the surface) to go to completion. This method will help to inhibit any artifacts resulting from "beading" of the solution as the formation of the self-assembling monolayer of silane progresses in the presence of the first silane, and will also help inhibit formation of islands at the molecular level which might otherwise reduce the effective local concentration of hydroxyl terminated second silane (following boration and oxidation as described in U.S. Pat. No. 6,444,268).

Note that in both examples the atmosphere in the holding chamber is controlled to prevent excessive evaporation or surface contamination Also, if needed, the process of either example can be repeated to ensure adequate functionalization of the substrate surface with the second silane (as well as an appropriate concentration of the first silane to obtain the desired surface energy quality). The substrate resulting from either example may then be used to fabricate an array using drop deposition in an in situ or another process (for example, deposition of previously obtained probe moieties, such as polynucleotides or proteins). This may be done by depositing onto the continuous functionalized area on the substrate surface, drops containing the chemical probes or probe precursors at the multiple feature locations of the array to be fabricated, so that the probes or probe precursors bind to the linking agent at the feature locations. This step may be repeated at one or more features, particularly when the in situ method of fabricating biopolymers is used. Such methods and their chemistry are described in detail in the references cited in the "Background" section above, including for example U.S. Pat. Nos. 6,242,266, 6,232,072, 6,180,351, 6,171,797, 6,323,043, and U.S. patent application Ser. No. 09/302,898 filed Apr. 30, 1999 by Caren et al., and the references cited in them.

Use of the foregoing method provides a relatively uniform coating within a region easier than could be obtained by exposing the substrate to the silanes in a reaction chamber. Furthermore, when a reaction chamber is used in which the silanes are introduced as a volume of solution into the chamber to cover the substrate surface, flow characteristics within the chamber can result in variation of linker density over the surface. Such variations can lead to variations in probe density (versus the expected probe density) within a feature, across the array, and between arrays. This is particularly true where it may be desirable to inject the silanes into the solvent within the chamber, rather than as part of a solvent solution with which the chamber is filled, to reduce possible polymerization of the silanes. As substrates become larger, these problems with using a reaction chamber may become more severe. On the other hand, increases in substrate size in a method of the present invention will not have the same effect. Additionally, with a method of the present invention, unlike a reaction chamber, it is not necessary to functionalize an entire surface of the substrate. Instead, only those parts of a substrate surface on which arrays will be fabricated need to be functionalized. Other areas of the same substrate surface are then available for further reaction or use, such as for application of a silicon glue to form a gasket to retain a hybridization solution when mated with a cover, or for printing of bar codes 356 or fiducial marks 18. However, the present invention contemplates that other methods such as the reaction chamber, or dipping tanks for the different solutions, could alternatively be used.

Arrays of the present invention of a type already described above in connection with FIGS. 1-3, 5, 6, can be produced by depositing drops containing the same concentration of different biopolymers or biopolymer precursors (for example, biomonomers such as nucleoside phosphoramidites) onto the feature locations for the different arrays. Such procedures are disclosed in detail in US in, for example, U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. These references are incorporated herein by reference. Other drop deposition methods could also be used for array fabrication. Also, instead of drop deposition methods, photolithographic array fabrication methods may be used such as described in U.S. Pat. Nos. 5,599,695, 5,753,788, and 6,329,143. Interfeature areas need not be present particularly when the arrays are made by photolithographic methods as described in those patents.

One particular apparatus of the present invention for producing surface modified substrates and arrays according to a method of the present invention, is described in detail below. Additionally, an apparatus and methods for reading arrays according to the present invention are also described.

Apparatus for Producing Surface Modified Substrates and Arrays

Referring now to FIG. 7, an apparatus of the present invention which can execute a method of the present invention, is illustrated. This apparatus is configured for use with a large substrate 19 which will later be cut into individual substrates 10 of any of the array assemblies 15. Substrate 19 will therefore also be referred to as having surfaces 11a and 11b. The apparatus shown essentially has two sections, a first section on which a surface 11a of the substrate 19 can be functionalized, and a second section in which the array is fabricated on the functionalized surface of the substrate 19. While these two sections are shown as part of one apparatus in FIG. 7, it will be appreciated that they can be entirely separate with the first section preparing many functionalized substrates 19 which are forwarded to the fabrication section for array fabrication, with their possibly being one or more first sections and one or more second sections remote from each other.

The first section of the apparatus of FIG. 7 includes a first substrate station 70 which can retain a mounted substrate 19, a third transporter 70, a head retainer 76, and a first drop deposition system in the form of a stationary pulse jet head 78 system. Pulse jet head system 78 can include two or three pulse jet heads which deliver drops of the solvent, linking agent, and additional agent, onto surface 11a of substrate 19 all as already described, so as to functionalize that surface. Drops are delivered from the stationary pulse jet head 78 while substrate 19 is advanced beneath it by transporter 70, all under control of a processor 140. A suitable holding chamber (not shown) may also be provided for the purposes already described during such functionalization. A mechanical means (such as a robot arm) may be provided to transfer a substrate 19 from substrate station 10 to the holding chamber, and to a second substrate station 20 when functionalization of the surface 11a is complete.

The second section of the apparatus of FIG. 7 includes substrate station 20 (sometimes referenced as a "substrate holder") on which a substrate 19 can be mounted and retained. Pins or similar means (not shown) can be provided on substrate station 20 by which to approximately align substrate 19 to a nominal position thereon (with alignment marks 18 on substrate 19 being used for more refined alignment). Substrate station 20 can include a vacuum chuck connected to a suitable vacuum source (not shown) to retain a substrate 19 without exerting too much pressure thereon, since substrate 19 is often made of glass. A flood station 68 is provided which can expose the entire surface of substrate 19, when positioned at station 68 as illustrated in broken lines in FIG. 7, to a fluid typically used in the in situ process, and to which all features must be exposed during each cycle (for example, oxidizer, deprotection agent, and wash buffer). In the case of deposition of a previously obtained polynucleotide, flood station 68 need not be present.

A second drop deposition system is present in the form of a dispensing head 210 which is retained by a head retainer 208. As mentioned above though, the head system can include more than one head 210 retained by the same head retainer 208 so that such retained heads move in unison together. The transporter system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 19) facing the dispensing head 210, by moving it in the direction of axis 63, while transporter 100 is used to provide adjustment of the position of head retainer 208 (and hence head 210) in a direction of axis 204 (and therefore move head 210 in the direction of travel 204a which is one direction on axis 204). In this manner, head 210 can be scanned line by line along parallel lines in a raster fashion, by scanning along a line over substrate 19 in the direction of axis 204 using transporter 100, while line to line transitioning movement of substrate 19 in a direction of axis 63 is provided by transporter 60. Transporter 60 can also move substrate holder 20 to position substrate 19 in flood station 68 (as illustrated by the substrate 19 shown in broken lines in FIG. 7). Head 210 may also optionally be moved in a vertical direction 202, by another suitable transporter (not shown) and its angle of rotation with respect to head 210 also adjusted. It will be appreciated that other scanning configurations could be used during array fabrication. It will also be appreciated that both transporters 60 and 100, or either one of them, with suitable construction, could be used to perform the foregoing scanning of head 210 with respect to substrate 19. Thus, when the present application recites "positioning", "moving", or similar, one element (such as head 210) in relation to another element (such as one of the stations 20 or substrate 19) it will be understood that any required moving can be accomplished by moving either element or a combination of both of them. The head 210, the transporter system, and processor 140 together act as the deposition system of the apparatus. An encoder 30 communicates with processor 140 to provide data on the exact location of substrate station 20 (and hence substrate 19 if positioned correctly on substrate station 20), while encoder 34 provides data on the exact location of holder 208 (and hence head 210 if positioned correctly on holder 208). Any suitable encoder, such as an optical encoder, may be used which provides data on linear position.

Processor 140 also has access through a communication module 144 to a communication channel 180 to communicate with a remote station. Communication channel 180 may, for example, be a Wide Area Network ("WAN"), telephone network, satellite network, or any other suitable communication channel.

Each of one or more heads 210 may be of a type similar to that used in an ink jet type of printer and may, for example, include five or more chambers (at least one for each of four nucleoside phosphoramidite monomers plus at least one for an activator solution) each communicating with a corresponding set of multiple drop dispensing orifices and multiple ejectors which are positioned in the chambers opposite respective orifices. Each ejector is in the form of an electrical resistor operating as a heating element under control of processor 140 (although piezoelectric elements could be used instead). Each orifice with its associated ejector and portion of the chamber, defines a corresponding pulse jet. It will be appreciated that head 210 could, for example, have more or less pulse jets as desired (for example, at least ten or at least one hundred pulse jets, with their nozzles organized in rows and columns). Application of a single electric pulse to an ejector will cause a droplet to be dispensed from a corresponding orifice. Certain elements of the head 210 can be adapted from parts of a commercially available thermal inkjet print head device available from Hewlett-Packard Co. as part no. HP51645A. A suitable head construction is described in U.S. Pat. No. 6,461,812, incorporated herein by reference. Alternatively, multiple heads could be used instead of a single head 210, each being similar in construction to head 210 and being movable in unison by the same transporter or being provided with respective transporters under control of processor 140 for independent movement. In this alternate configuration, each head may dispense a corresponding biomonomer (for example, one of four nucleoside phosphoramidites) or an activator solution.

Each head of head system 78 may also be of a type similar to that of each head 210, as already described. However, since each head will deliver only liquid drops of one type (solvent, or one of the two silanes) each head need only have one chamber to provide fluid to all the pulse jets of that head.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As discussed above, when the orifice is in motion with respect to the substrate surface at the time an ejector is activated, the actual site of deposition of the material will not be the location that is at the moment of activation perpendicularly aligned with an orifice. However, the actual deposited location will be predictable for the given distances and velocities.

The apparatus further includes a display 310, speaker 314, and operator input device 312. Operator input device 312 may, for example, be a keyboard, mouse, or the like. Processor 140 has access to a memory 141, and controls print head system 78 and print head 210 (specifically, the activation of the ejectors therein), operation of the transporter system and the third transporter 72, and operation of display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the steps required by the present invention, or any hardware or software combination which will perform those or equivalent steps. The programming can be provided remotely to processor 141 through communication channel 180, or previously saved in a computer program product such as memory 141 or some other portable or fixed computer readable storage medium using any of those devices mentioned below in connection with memory 141. For example, a magnetic or optical disk 324a may carry the programming, and can be read by disk writer/reader 326. A cutter 152 is provided to cut substrate 19 into individual array assemblies 15.

Operation of the Apparatus

The operation of the apparatus of FIG. 7 will now be described. In a first step of the sequence, a substrate surface may be produced with surface regions of different linker agent density (and different capping agent density, as discussed above). It will be assumed that a substrate 19 is already mounted on substrate station 70. In this case the substrate is functionalized using the toluene/water solvent, and first and second silanes, in accordance with the method already described. To accomplish this transporter system 72 advances the mounted substrate 19 beneath head system 78 while drops of solvent are deposited to provide the continuous layer of solvent with no gaps, as already described. This process can be repeated but with drops containing the second silane then being deposited. The first silane may be included in the drops with the second silane or the foregoing can be repeated in the case where the first silane is delivered as drops of a separate solution. The substrate may be transferred to the holding chamber between the second and first silane (if separate) and following application of both, using a robot arm or manually by an operator, in accordance with the method as already described.

At this point preparation of the functionalized surface 11a is complete.

The substrate 19 with the functionalized surface 11a may then be transferred to the substrate station 20 either manually or by the robot arm, as which station one or more arrays will be fabricated on the substrate surface 11a with features in one region repeated in another different region at a different feature probe density, copy number, etc. In this sequence it will be assumed that processor 140 is programmed with the necessary layout information to fabricate target arrays 12. Using information such as the foregoing target layout and the number and location of drop dispensers in head 210, processor 140 can then determine a reagent drop deposition pattern. Alternatively, such a pattern could have been determined by another processor (such as a remote processor) and communicated to memory 141 through communication channel 180 or by forwarding a portable storage medium carrying such pattern data for reading by reader/writer 326. Processor 140 controls fabrication, in accordance with the deposition pattern, to generate the one or more arrays 12 on each section of substrate 19 which will later be cut into each substrate 10, by depositing for each target feature during each cycle, a reagent drop set as previously described. This is repeated at each of the different desired regions on the surface 11a for a substrate 10 (for example, the regions at each of the regions at which arrays 12a, 12b, 12c, 12d will be formed) so that the probe or probe precursors bind to the different regions through the linker agent. The foregoing sequence is repeated for each cycle of the in situ fabrication process. Drops are deposited from the head while moving along each line of the raster during scanning. No drops are dispensed for features or otherwise during line transitioning. Processor 140 also sends substrate 19 to flood station 68 for cycle intervening or final steps as required, all in accordance with the conventional in situ polynucleotide array fabrication process described above.

As a result of the above, multiple array assemblies are formed on each section which will be cut to form a substrate 10, so as to form the array thereon with features of different probe composition in a region which features are repeated in another region but with a different probe density, copy number, etc.

The substrate 19 may then be sent to a cutter 152 wherein sections of substrate 19 are separated into substrates 10 carrying one ore more arrays 12, to provide multiple array assemblies 15. One or more array assemblies 15 may then be forwarded to one or more remote users. Processor 140 also causes deposition of drops from all multi-dispenser drop groups to be deposited at separate test locations, such as at a test pattern 250 which may be separate from arrays 12 as already described above. The foregoing array fabrication sequence can be repeated at the fabrication station as desired for multiple substrates 19 in turn.

During array fabrication errors can be monitored and used in any of the manners described in U.S. Patent Application "Polynucleotide Array Fabrication" by Caren et al., Ser. No. 09/302,898 filed Apr. 30, 1999, and U.S. Pat. No. 6,232,072, the disclosures of which are herein incorporated by reference. Also, the one or more identifiers in the form of bar codes 356 can be attached or printed onto sections of substrate 19 defining the substrates 10 before entering, or after leaving, first fabrication station 70, or after leaving the second fabrication station 20. If bar codes 356 are present before entering first fabrication station 70 they can include an indication of the location of different regions on a substrate to which probes or probe precursors will bind with different density, copy number, etc. They can then be read by a bar code reader (not shown) in the first fabrication station, and received by processor 140 to then control the drop deposition system to form the one or more arrays with features of different probe composition in one of the regions which are repeated in another of the regions at a different feature probe density, copy number, etc. If bar codes 356 are present before substrate 190 enters second substrate station 20, they can be read by a bar code reader (not shown) in the second substrate station and used by processor 140 to determine the different regions at which features are to be repeated with a same probe composition which processor 140 will then form in second substrate station 20. Any of the foregoing types of information on the different regions can be contained within the bar codes 356 (or other identifiers) or in a file previously linked to them. Regardless of the foregoing, at any point in the operation of the apparatus of FIG. 7, processor 140 will associate (540) each array with an identifier such as a bar code 356, which identifier carries an indication of the different feature probe densities, copy number, etc., of the same probe composition or is linked to a file carrying such information. The file and linkage can be stored by processor 140 and saved into memory 141 or can be written onto a portable storage medium 324b which is then placed in the same package 340 as the corresponding array assembly 15 for shipping to a remote customer. The actual indication can take many forms. For example, one or more of the bar codes 356 associated with the arrays on the same substrate 10, may specify that one array 12a is the same as another array such as array 12c, but that one the region carrying one has a feature probe density and/or probe copy number, etc., which is a proportion of the region at the other (for example, the feature probe density of array 12c is 20% that of array 12a). Alternatively, absolute feature probe density numbers may be provided for each array in its associated bar code 356.

Optionally other characteristics of the fabricated arrays can be included in the code 356 applied to the array substrate or a housing, or a file linkable to such code, in a manner as described in the foregoing patent application and U.S. Pat. No. 6,180,351. As mentioned above, these references are incorporated herein by reference.

Array Reading Apparatus

Figure 8:
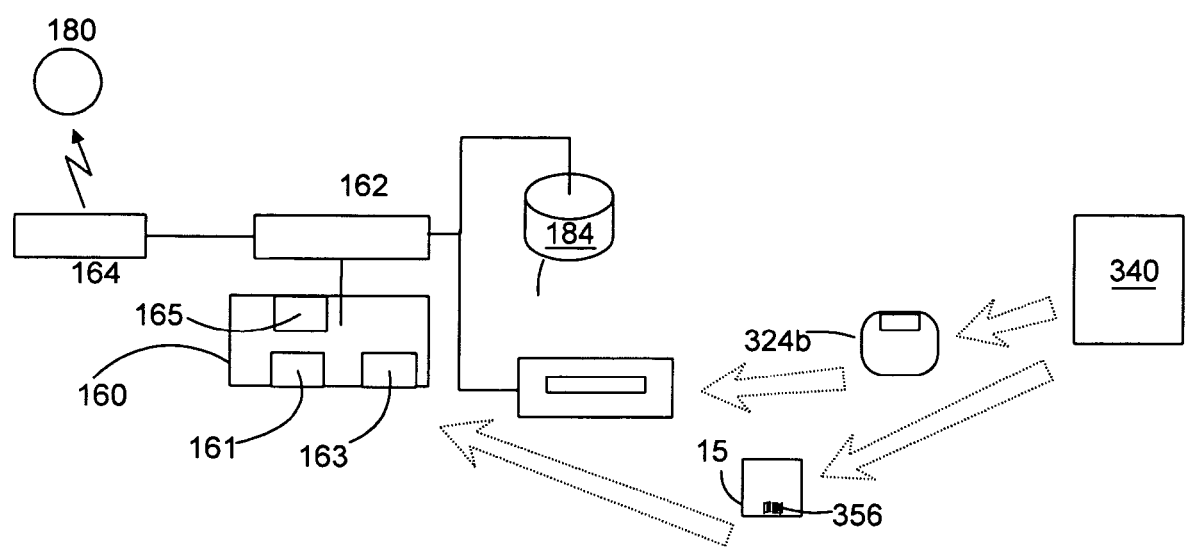
FIG. 8 illustrates an array reader that may be used in accordance with the subject invention.

FIG. 8 illustrates an array reader at a single "user station", which is likely to be (but not necessarily) remote from the fabrication station of FIG. 7 (usually the user station is at the location of the customer which ordered the received array 12). The user station includes a processor 162, a memory 184, a scanner 160 which can read an array, data writer/reader 186 (which may be capable of writing/reading to the same type of media as writer/reader 326), and a communication module 164 which also has access to communication channel 180. Processor 162 is programmed to perform all the functions required of it. Scanner 160 may include a holder 161 which receives and holds an array assembly in the form of an array unit 18 or in the form of web 10 carrying arrays 12, as well as a source of illumination (such as a laser) and one or more light sensors 165 to read fluorescent light signals from respective features on the array as signal data which is obtained by processor 162 from the light sensor. Scanner 160 also includes a reader 163 to read a bar code 356 appearing on array assembly 15. Processor 162 is also capable of identifying signal data from read features 16 of a same probe composition with different feature probe densities, based on the read indication from a read bar code 163, and merging signal data from such in a manner further described below.

Communication module 164 may be any type of suitable communication module, such as those described in connection with communication module 144. Memory 184 can be any type of memory such as those used for memory 141. Scanner 160 can be any suitable apparatus for reading an array, such as one which can read the location and intensity of fluorescence at each feature of an array following exposure to a fluorescently labeled sample. For example, such a scanner may be similar to the DNA MICROARRAY SCANNER available from Agilent Technologies, Inc. Palo Alto, Calif. Other suitable apparatus and methods are described in U.S. patent applications: Ser. No. 09/846,125 "Reading Multi-Featured Arrays" by Dorsel et al.; and U.S. Pat. No. 6,406, 849. The scanning components of scanner 160, holder 161, and reader 163 may all be contained within the same housing of a single same apparatus.

It will be understood that there may be multiple user stations such as shown in FIG. 8, each remote from the fabrication station and each other, in which case the fabrication station acts as a central fabrication station (that is, a fabrication station which services more than one remote user station at the same or different times). One or more such user stations may be in communication with the fabrication station at any given time. It will also be appreciated that processors 140 and 162 can be programmed from any computer readable medium carrying a suitable computer program. For example, such a medium can be any memory device such as those described in connection with memory 141, and may be read locally (such as by reader/writer 320 in the case of processor 140 or writer/reader 186 in the case of processor 162) or from a remote location through communication channel 180.

Biopolymeric Arrays Having Features Based on Target Abundance

Also provided by the subject invention are arrays of nucleic acids (e.g., oligonucleotides, polynucleotides), peptides (e.g., polypeptides, proteins, antibodies) or other molecules capable of binding with target biomolecules in a solution (e.g., nucleic acids, proteins, etc.), which arrays have features customized or tailored with respect to the at least anticipated abundance of a target in a sample for which the array is designed to assay. That is, an array of probes (i.e., binding agents or members of a binding pair in this context) covalently bonded to a substrate surface in the form of an "array" or pattern is provided where certain parameters of the array have been tailored to the amount of a particular target present or suspected of being present in a sample for which the array is designed to assay. Such arrays find use in a variety of different fields, e.g., genomics (in sequencing by hybridization, SNP detection, differential gene expression analysis, identification of novel genes, gene mapping, finger printing, mutations analysis, etc.), proteomics, and the like.

The subject arrays include at least two distinct polymers, e.g., that differ by monomeric sequence, attached to different and known locations on the substrate surface. Each distinct polymer of the array is typically present as a composition of multiple copies of the polymer on a substrate surface, e.g., as a spot or feature on the surface of the substrate. The number of distinct polymeric sequences, and hence spots or similar structures, present on the array may vary, where a typical array may contain more than about ten, more than about one hundred, more than about one thousand, more than about ten thousand or even more than about one hundred thousand features, e.g., in an area of less than about 20 $cm^2$ or even less than about 10 $cm^2$ or less. For example, features may have widths (that is, diameter, for a round spot) in the range from about 10 μm to about 1.0 cm. In other embodiments, each feature may have a width in the range from about 1.0 μm to about 1.0 mm, e.g., from about 5.0 μm to about 500 μm, e.g., from about 10 μm to about 200 μm. Non-round features may have area ranges equivalent to that of circular features with the foregoing width (diameter) ranges. At least some, or all, of the features are of different compositions (for example, when any repeats of each feature composition are excluded, the remaining features may account for at least about 5%, 10% or 20% of the total number of features). In the case where arrays are formed by the conventional in situ or deposition of previously obtained moieties, as described above, by depositing for each feature a droplet of reagent in each cycle such as by using a pulse jet such as an inkjet type head, interfeature areas will typically (but not essentially) be present which do not carry any polynucleotide (see for example interfeature areas 17 of FIG. 2). It will be appreciated though, that the interfeature areas could be of various sizes and configurations. It will also be appreciated that there need not be any space separating arrays from one another (for example, when arrays are fabricated using light directed techniques). For example, such interfeature areas may be present where the arrays are formed by processes involving drop deposition of reagents, but may not be present when, for example, photolithographic array fabrication process are used. Each feature carries a predetermined polynucleotide (which includes the possibility of mixtures of polynucleotides). The spots or features of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like.

The array substrate may also include one or more identifiers in the form of bar codes. Identifiers such as other optical or magnetic identifiers could be used instead of bar codes which will carry the information discussed above. Each identifier may be associated with its corresponding array by being positioned adjacent that array. However, this need not be the case and identifiers such as bar code can be positioned elsewhere on substrate if some other means of associating each bar code with its corresponding array is provided (for example, by relative physical locations). Further, a single identifier might be provided which is associated with more than one array on a same substrate and such one or more identifiers may be positioned on a leading or trailing end of substrate. The substrate may further have one or more fiducial marks for alignment purposes during array fabrication.

In the broadest sense, the arrays are arrays of polymeric or biopolymeric ligands or molecules, i.e., binding agents. In many embodiments of interest, the arrays are arrays of nucleic acids, including oligonucleotides, polynucleotides, cDNAs, mRNAs, synthetic mimetics thereof, and the like.

Each array may cover an area of less than about 100 cm$^2$, or even less than about 50 cm$^2$, 10 cm$^2$ or 1 cm$^2$. In many embodiments, the substrate carrying the one or more arrays will be shaped generally as a rectangular solid (although other shapes are possible), having a length of more than about 4 mm and less than about 1 m, usually more than about 4 mm and less than about 600 mm, more usually less than about 400 mm; a width of more than about 4 mm and less than about 1 m, usually less than about 500 mm and more usually less than about 400 mm; and a thickness of more than about 0.01 mm and less than about 5.0 mm, usually more than about 0.1 mm and less than about 2 mm and more usually more than about 0.2 and less than about 1 mm. When the array substrate is flexible, it may be of various lengths including at least about 1 m, at least about 2 m, or at least about 5 m (or even at least about 10 m). With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least about 20%, or about 50% (or even at least about 70%, 90%, or 95%), of the illuminating light incident on the substrate as may be measured across the entire integrated spectrum of such illuminating light or alternatively at 532 nm or 633 nm.

In a variation of the embodiments above, it is possible that each array assembly 15 may be contained with a suitable housing. Such a housing may include a closed chamber accessible through one or more ports normally closed by septa, which carries the substrate 10. In this case, the identifier for all arrays on a substrate 10 can be associated with them by being applied to the housing. It will also be appreciated that arrays may be read by any other method or apparatus than that described above, with other reading methods including other optical techniques (for example, detecting chemiluminescent or electroluminescent labels) or electrical techniques (where each feature is provided with an electrode to detect hybridization at that feature in a manner disclosed in U.S. Pat. Nos. 6,251,685, 6,221,583 and elsewhere). As to retrieving signal data from features ("feature extraction") in which features and their corresponding signals are identified in an image of a read array, this can be performed using procedures such as described in U.S. patent application Ser. Nos. 09/589,046, 09/659,415 and 10/086,839, all under the title "Method And System For Extracting Data From Surface Array Deposited Features".

A feature of the subject biopolymeric arrays is that one or more aspects of the array have been determined according to the amount of target present or suspected of being present in a sample for which the array is designed to assay. As described above, such aspects which have been designed to account for target amount include, but are not limited to, the copy number of a given probe, the density of a feature that includes the copies of a given probe, the number of replicate features that include the copies of a given probe, and the like.

Utility

The subject arrays find use in a variety of different applications, where such applications are generally analyte detection applications in which the presence of a particular analyte (i.e., target) in a given sample is detected at least qualitatively, if not quantitatively. Protocols for carrying out such assays are well known to those of skill in the art and need not be described in great detail here. Generally, the sample suspected of containing the analyte of interest is contacted with an array produced according to the subject methods under conditions sufficient for the analyte to bind to its respective binding pair member (i.e., probe) that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface. Specific analyte detection applications of interest include, but are not limited to, hybridization assays in which nucleic acid arrays are employed.

In these assays, a sample to be contacted with an array may first be prepared, where preparation may include labeling of the targets with a detectable label, e.g. a member of signal producing system. Generally, such detectable labels include, but are not limited to, radioactive isotopes, fluorescers, chemiluminescers, enzymes, enzyme substrates, enzyme cofactors, enzyme inhibitors, dyes, metal ions, metal sols, ligands (e.g., biotin or haptens) and the like. Thus, at some time prior to the detection step, described below, any target analyte present in the initial sample contacted with the array may be labeled with a detectable label. Labeling can occur either prior to or following contact with the array. In other words, the analyte, e.g., nucleic acids, present in the fluid sample contacted with the array may be labeled prior to or after contact, e.g., hybridization, with the array. In some embodiments of the subject methods, the sample analytes e.g., nucleic acids, are directly labeled with a detectable label, wherein the label may be covalently or non-covalently attached to the nucleic acids of the sample. For example, in the case of nucleic acids, the nucleic acids, including the target nucleotide sequence, may be labeled with biotin, exposed to hybridization conditions, wherein the labeled target nucleotide sequence binds to an avidin-label or an avidin-generating species. In an alternative embodiment, the target analyte such as the target nucleotide sequence is indirectly labeled with a detectable label, wherein the label may be covalently or non-covalently attached to the target nucleotide sequence. For example, the label may be non-covalently attached to a linker group, which in turn is (i) covalently attached to the target nucleotide sequence, or (ii) comprises a sequence which is complementary to the target nucleotide sequence. In another example, the probes may be extended, after hybridization, using chain-extension technology or sandwich-assay technology to generate a detectable signal (see, e.g., U.S. Pat. No. 5,200,314).

In certain embodiments, the label is a fluorescent compound, i.e., capable of emitting radiation (visible or invisible) upon stimulation by radiation of a wavelength different from that of the emitted radiation, or through other manners of excitation, e.g. chemical or non-radiative energy transfer. The label may be a fluorescent dye. Usually, a target with a fluorescent label includes a fluorescent group covalently attached to a nucleic acid molecule capable of binding specifically to the complementary probe nucleotide sequence.

Following sample preparation (labeling, pre-amplification, etc.), the sample may be introduced to the array using any convenient protocol, e.g., sample may be introduced using a pipette, syringe or any other suitable introduction protocol. The sample is contacted with the array under appropriate conditions to form binding complexes on the surface of the substrate by the interaction of the surface-bound probe molecule and the complementary target molecule in the sample. The presence of target/probe complexes, e.g., hybridized complexes, may then be detected. In the case of hybridization assays, the sample is typically contacted with an array under stringent hybridization conditions, whereby complexes are formed between target nucleic acids that agent are complementary to probe sequences attached to the array surface, i.e., duplex nucleic acids are formed on the surface of the substrate by the interaction of the probe nucleic acid and its complement target nucleic acid present in the sample. An example of stringent hybridization conditions is hybridization at about 50° C. or higher and 0.1×SSC (15 mM sodium chloride/1.5 mM sodium citrate). Another example of stringent hybridization conditions is overnight incubation at about 42° C. in a solution: 50% formamide, 5×SSC (150 mM NaCl, 15 mM trisodium citrate), 50 mM sodium phosphate (pH7.6), 5× Denhardt's solution, 10% dextran sulfate, followed by washing the arrays in 0.1×SSC at about 65° C. Hybridization involving nucleic acids generally takes from about 30 minutes to about 24 hours, but may vary as required. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions, including less stringent conditions, are known in the art and may also be employed as appropriate, as well as other less stringent conditions.

The array is then incubated with the sample under appropriate array assay conditions, e.g., hybridization conditions, as mentioned above, where conditions may vary depending on the particular array and binding pair.

Once the incubation step is complete, the sample evaluation array is washed at least one time to remove any unbound and non-specifically bound sample from the substrate, generally at least two wash cycles are used. Washing agents used in array assays are known in the art and, of course, may vary depending on the particular binding pair used in the particular assay. For example, in those embodiments employing nucleic acid hybridization, washing agents of interest include, but are not limited to, salt solutions such as sodium, sodium phosphate (SSP) and sodium, sodium chloride (SSC) and the like as is known in the art, at different concentrations and which may include some surfactant as well.

Following the washing procedure, the sample evaluation array is then interrogated or read to detect any resultant surface bound binding pair or target/probe complexes, e.g., duplex nucleic acids, to obtain signal data related to the presence of the surface bound binding complexes, i.e., the label is detected using colorimetric, fluorimetric, chemiluminescent, bioluminescent means or other appropriate means. The obtained signal data from the reading may be in any convenient form, i.e., may be in raw form or may be in a processed form.

As such, in using an array made by the method of the present invention, the array will typically be exposed to a sample (for example, a fluorescently labeled analyte, e.g., protein containing sample) and the array then read. Reading of the array to obtain signal data may be accomplished by illuminating the array and reading the location and intensity of resulting fluorescence (if such methodology was employed) at each feature of the array to obtain a result. For example, an array scanner may be used for this purpose that is similar to the Agilent MICROARRAY SCANNER available from Agilent Technologies, Palo Alto, Calif. Other suitable apparatus and methods for reading an array to obtain signal data are described in U.S. patent application Ser. Nos: 09/846,125 "Reading Multi-Featured Arrays" by Dorsel et al.; and Ser. No. 09/430,214 "Interrogating Multi-Featured Arrays" by Dorsel et al., the disclosures of which are herein incorporated by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583, the disclosure of which is herein incorporated by reference, and elsewhere).

In those embodiments having replicate features, e.g., the subject invention also scanning or reading the array to obtain information related to the features of the array, determining replicate features of the array and extracting information from the replicate features, e.g., by excluding an non-replicate features, combining the information from the replicates in a meaningful manner to obtain information representative of the target bound to the replicates, e.g., a median signal intensity value may be determined from replicate features. Methods and systems for extracting data from surface array deposited features that may be adapted for use in the subject invention include those described in U.S. Pat. No. 6,591,196, the disclosure of which is herein incorporated by reference.

Furthermore, information about the design of the array and/or information about a particular sample or target thereof may be incorporated into future array designs. Information such as the number of probe copies, feature number, feature density feature size, the distances between features, and the signals obtained from various array designs may be used to make subject algorithms more robust. The subject algorithms may be iterated, each time changing one or more of the array design parameters, e.g., based on previous array assay results, until the signals obtained from an array meets predetermined criteria such as design specifications and the like.

In certain embodiments, the results of the array reading (processed or not) may be forwarded (such as by communication) to a remote location if desired, and received there for further use (such as further processing). By "remote location" is meant a location other than the location at which the sample evaluation device is present and sample evaluation occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, Internet, etc.

As noted above, the arrays produced according to the subject method may be employed in a variety of array assays including hybridization assays. Specific hybridization assays of interest which may be practiced using the subject arrays include: gene discovery assays, differential gene expression analysis assays; nucleic acid sequencing assays, and the like. Patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Other array assays of interest include those where the arrays are arrays of polypeptide binding agents, e.g., protein arrays, where specific applications of interest include analyte detection/proteomics applications, including those described in U.S. Pat. Nos. 4,591,570; 5,171,695; 5,436,170; 5,486,452; 5,532,128; and 6,197,599; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

For example, embodiments may include using an array prepared with respect to the at least suspected abundance of a target in a sample to which the array is designed to assay at the user station of FIG. 8, by receiving the package 340 (580) from the remote fabrication station and manually opening it to retrieve an array assembly 15 and portable storage medium 324b (if any was present in package 340). A contiguous layer of a sample, for example a test sample, may be exposed to the one or more arrays 12 on the received array assembly 15 in a known manner under known conditions. Apparatus and procedures for hybridization are described, for example, in U.S. Pat. No. 6,258,593 and 6,399,394. In one configuration, a separate drop of each target containing solution may be placed on each circular array in the embodiment of FIG. 6. Following hybridization and washing in a known manner, the array unit 18 may then be inserted into holder 161 in scanner 160 and read (600) by it to obtain read results (such as signal data representing the fluorescence pattern on the array 12). The reader 163 in scanner 160 may also read the identifier 356 present on the array assembly 15 in association with the corresponding array 12, while the array unit 18 is still positioned in retained in holder 161 or beforehand. Using identifier 356, processor 162 may then retrieve (580) the characteristic data for one or more arrays 12 from portable storage medium 324b or from the database of such information in memory 141 by communicating the map identifier to that database through communication module 164 and communication channel 180 and receiving the corresponding identity map in response. Such characteristic data may include the indication of features of different probe densities, copy number, etc. of a same probe composition as discussed above or of like features. For example, data may include data from different features of the same probe composition that are replicates.

The resulting retrieved characteristic data for an array may be used to either control reading of the array or to process information obtained from reading the array. For example, the customer may decide (through providing suitable instructions to processor 162) that a particular feature need not be read or the data from reading that feature may be discarded, since the polynucleotide sequence at that feature is not likely to produce any reliable data under the conditions of a particular sample hybridization. However, processor 162 uses the retrieved indication of features of different probe densities of a same probe composition, to identify signal data from features of a same probe composition with different probe densities or may use retrieved indication of replicate features to identify signal data from replicate features. With such signal data identified, e.g., replicate feature signal data or the like, processor 162 can then merge (640) signal data from features identified to be of the same probe composition but with different probe densities or from features identified to be of replicate features. This merging can take place according to any suitable routine which may be preprogrammed into processor 162 by a user, or retrieved from portable storage medium 324b or remotely from memory 141 based on a read bar code 356 (or other identifier) for the one or more arrays being read. In one routine, signal data from a feature of higher probe density which is greater than some predetermined signal (for example, 90% or 95% of the maximum signal which can be read from such a feature by the reader), may be rejected in favor of the signal data from a feature of a same probe composition of lower feature probe density provided it is greater than some predetermined signal (for example at least 5% or 10% of the maximum signal which can be read from such a feature by the reader). If signals from multiple features of a same probe composition are all within predetermined minimum and maximum values, then some statistical representation (for example, an average signal) can be calculated from all of such signals.

Results from the array reading can be further processed results, such as obtained by rejecting a reading for a feature which is below a predetermined threshold and/or forming conclusions based on the pattern read from the array (such as whether or not a particular target sequence may have been present in the sample). The results of the reading (processed or not) can be forwarded (such as by communication) to be received at a remote location for further evaluation and/or processing, or use, using communication channel 180 or reader/writer 186 and medium 190. This data may be transmitted by others as required to reach the remote location, or re-transmitted to elsewhere as desired.

Computer-Related Embodiments

Also provided by the subject invention are algorithms stored on computer readable medium. The subject algorithms may be employed in the practice of one or more aspects of the subject invention. For example, embodiments include algorithms for preparing an array in accordance with the subject invention, e.g., receiving information about target abundance and determining appropriate array parameters based on this information and/or directing an array fabrication device to fabricate an array according to such information. Embodiments also include algorithms for obtaining or extracting information from a subject array once it has been used in an array assay.

More specifically, arrays may be designed manually or with the assistance of a computing means, in which an algorithm is employed that is capable of directing suitable software/hardware means to prepare an array with respect to the amount of target present or suspected of being present in a sample. Typically, the algorithm is recorded on a computer readable storage medium, where such media are well known to those of skill in the art. More specifically, one or more aspects of the subject invention may be in the form of computer readable media having an algorithm, e.g., computer programming, stored thereon for implementing some or all of the subject methods. For example, the number of copies of a given probe and/or feature number and/or copy density may be determined using an algorithm in conjunction with a computational analysis system. In certain embodiments, the algorithm may be iterative as will be described in greater detail below.

Accordingly, embodiments of the subject invention include computer readable media having programming (also known as computer control logic) stored thereon for implementing the steps required to determine the appropriate probe copy number and/or feature density and/or feature number from data related to the amount of target in or suspected of being in a sample. The computer readable media may be, for example, in the form of a computer disk or CD, a floppy disc, a magnetic "hard card", a server, or any other computer readable media capable of containing data or the like, stored electronically, magnetically, optically or by other means. Stored programming embodying steps for determining the appropriate probe copy number and/or feature density and/or feature number may be transferred to a computer such as a personal computer (PC), (i.e., accessible by a researcher or the like), or even to an array fabrication device such as a fluid deposition device (e.g., a pulsejet fluid deposition device (see for example U.S. Pat. Nos. 6,458,583 and 6,323,043, the disclosures of which are herein incorporated by reference)) by physical transfer of a CD, floppy disk, or like medium, or may be transferred using a computer network, server, or other interface connection, e.g., the Internet.

In certain embodiments of the subject invention, a system of the invention may include a computer or the like with a stored algorithm capable of carrying out array design methods, i.e., a computational analysis system. In certain embodiments, the system is further characterized in that it provides a user interface, where the user interface presents to a user the option of selecting among one or more different, including multiple different, inputs, e.g., various parameter values for the algorithm. Computational systems that may be readily modified to become systems of the subject invention include those described in U.S. Pat. No. 6,251,588; the disclosure of which is herein incorporated by reference.

Algorithms for obtaining and/or processing information related to the features of an array are also provided. As noted above, such algorithms may be present on a computer readable medium, as described above. These algorithms are programs that direct suitable computing means to obtain data from replicate features and combine the date together in an appropriate manner to obtain information about the target bound to the replicate features. For example, as noted above, a scanning component that produces images of an array representing intensities of data signals emitted from discrete positions of the array may be employed to scan or read a subject array. Accordingly, in order to extract relevant data from the array, a computer program, embodied on a computer readable medium, may be employed with suitable computing means, e.g., a computer, for executing the computer program. The program processes images of an array produced by the scanning component to select features in the images of the array corresponding to molecules bound to replicate features of the array and that extracts data from the replicate features within images of the array. Accordingly, the algorithm enables data from replicate features to be combined in a useable manner.

For example, embodiments include a method embodied in a computer program for extracting data from a biopolymeric array having features designed at least in part on target abundance. Such a method may include receiving a number of images of the array, each produced by scanning the array to determine intensities of data signals emanating from discrete positions of the array corresponding to replicate features (e.g., fluorescent emission from fluorophores incorporated into molecules bound to features of the molecular array, radiation emitted by radioisotopes incorporated into molecules bound to features of the molecular array, and light emission from chemiluminescent moieties incorporated into molecules bound to features of the molecular array). Each image of the number of images includes an array of pixels, each pixel having a data signal intensity value. The method may include determining a median intensity value and standard deviation of intensity values (or other meaningful value) of pixels for the pixels corresponding to replicate feature.

Kits

Finally, kits for use in practicing the subject invention are also provided. The subject kits at least include one or more subject biopolymeric arrays. In other words, embodiments of the subject invention include kits that have one or more biopolymeric arrays having at least one biopolymeric array comprising at least a first population of a number of copies of a first probe for a first target immobilized on a surface of a solid support, wherein the number of probe copies is dependant on the abundance of the target present or suspected of being present in a sample.

The kits may further include one or more additional components necessary for carrying out an analyte detection assay, such as sample preparation reagents, buffers, labels, and the like. As such, the kits may include one or more containers such as vials or bottles, with each container containing a separate component for the assay, and reagents for carrying out an array assay such as a nucleic acid hybridization assay or the like. The kits may also include a denaturation reagent for denaturing the analyte, buffers such as hybridization buffers, wash mediums, enzyme substrates, reagents for generating a labeled target sample such as a labeled target nucleic acid sample, negative and positive controls.

In addition to one or more biopolymeric arrays, the subject kits may also include written instructions for using the biopolymeric arrays in array assays such as hybridization assays or protein binding assays. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

The kits may further include one or more additional components necessary for carrying out an array assay, e.g., a hybridization assay or protein binding assay, where such may include sample preparation reagents, buffers, labels, and the like. As such, the kits may include one or more containers such as vials or bottles, with each container containing a separate component for the array assay, and reagents for carrying out an array assay such as a nucleic acid hybridization assay, protein binding assay, or the like. The kits may also include a denaturation reagent for denaturing an analyte, buffers such as hybridization buffers, wash mediums, enzyme substrates, reagents for generating a labeled target sample such as a labeled target nucleic acid sample, negative and positive controls.

The subject kit may also include one or more algorithms, as described above, present on computer readable medium, or means for accessing such algorithms such as means for obtaining the algorithms from a remote source, e.g. via the Internet.

In many embodiments of the subject kits, the components of the kit are packaged in a kit containment element to make a single, easily handled unit, where the kit containment element, e.g., box or analogous structure, may or may not be an airtight container, e.g., to further preserve the one or more biopolymeric arrays and reagents, if present, until use.

It is evident from the above results and discussion that the above-described invention provides biopolymeric arrays, and method of producing such biopolymeric arrays, that may be tailored to effectively be used with targets present in a range of amounts in a sample. Accordingly, meaningful information may be obtained when the subject biopolymeric arrays are used in array assays with very low, low, average, high and very high abundance targets. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for fabricating an array, comprising:
    grouping probes into a plurality of ranked groups of probes, wherein probes that detect lower abundance targets in a sample are grouped into a higher ranked group and probes that detect higher abundance targets in said sample are grouped into a lower ranked group;
    designing an array comprising said ranked groups of probes, wherein said array comprises less replicates of features comprising probes in said higher ranked group as compared to probes of said lower ranked group of probes; and
    fabricating said array wherein said array comprises less replicates of features comprising said probes that detect lower abundance targets in said sample as compared to said probes that detect higher abundance targets in said sample.

2. The method of claim 1, wherein said probes that detect lower abundance targets in said sample and said probes that detect higher abundance targets in said sample are identified based on experimental data.

3. The method of claim 1, wherein said probes are grouped according to location, functional or expression.

4. The method of claim 1, wherein said probes are arbitrarily grouped.

5. The method of claim 1, wherein said probes are grouped by customer input.

6. The method of claim 1, wherein said probes are probes for detecting miRNA.

7. The method of claim 1, wherein said probes are for detecting messenger RNA expression.

8. The method of claim 1, wherein said probes are oligonucleotides.

9. The method of claim 1, wherein said oligonucleotides are 10-100 nucleotides in length.

10. The method of claim 8, wherein said fabricating comprises depositing said oligonucleotides on said array.

* * * * *